US011173282B2

(12) United States Patent
Chan et al.

(10) Patent No.: US 11,173,282 B2
(45) Date of Patent: Nov. 16, 2021

(54) CATHETER DEVICES WITH INTEGRATED TUBING MANAGEMENT MECHANISM AND RELATED METHODS

(71) Applicant: B. Braun Melsungen AG, Melsungen (DE)

(72) Inventors: Hwa Loon Chan, Melbourne (AU); Eng Keat Ong, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 725 days.

(21) Appl. No.: 15/737,940

(22) PCT Filed: Jul. 1, 2016

(86) PCT No.: PCT/EP2016/065490
§ 371 (c)(1),
(2) Date: Dec. 19, 2017

(87) PCT Pub. No.: WO2017/001656
PCT Pub. Date: Jan. 5, 2017

(65) Prior Publication Data
US 2018/0154112 A1    Jun. 7, 2018

Related U.S. Application Data

(60) Provisional application No. 62/188,000, filed on Jul. 2, 2015.

(51) Int. Cl.
*A61M 25/00* (2006.01)
*A61M 25/06* (2006.01)
*A61M 25/02* (2006.01)

(52) U.S. Cl.
CPC .... *A61M 25/0097* (2013.01); *A61M 25/0606* (2013.01); *A61M 2025/0035* (2013.01); *A61M 2025/024* (2013.01)

(58) Field of Classification Search
CPC .......... A61M 25/0097; A61M 25/0606; A61M 25/0637; A61M 25/0618; A61M 2025/0035; A61M 2025/024
See application file for complete search history.

(56) References Cited

U.S. PATENT DOCUMENTS 7,041,083 B2    5/2006  Chu et al.
8,668,674 B2    3/2014  White et al.
(Continued)

FOREIGN PATENT DOCUMENTS

CA    2798020    11/2011
CN    101448541 A    6/2009
(Continued)

OTHER PUBLICATIONS

International Preliminary Report on Patentability (Chapter I) on corresponding PCT application (PCT/EP 2016/065490) from International Searching Authority (EPO) dated Jan. 11, 2018.
(Continued)

*Primary Examiner* — Tiffany Legette
(74) *Attorney, Agent, or Firm* — Klein, O'Neill & Singh, LLP

(57) ABSTRACT

Catheter devices with a tube management system are described. The catheter devices can have a catheter hub, a port extending from the catheter hub, a needle hub, a septum for controlling fluid flow from the port to a distal opening of the catheter hub, and a flexible tubing extending from the port. A tube deflector at the port guides the flexible tubing from a closed position to an open position. Tube securing mechanisms formed on the catheter hub also guides the flexible tubing from the closed position to the open position. A needle guard is usable with the needle device to block a tip of the needle.

19 Claims, 10 Drawing Sheets

(56) References Cited

U.S. PATENT DOCUMENTS

| | | | |
|---|---|---|---|
| 8,771,230 B2 | 7/2014 | White et al. | |
| 8,814,833 B2 | 8/2014 | Farrell et al. | |
| 2002/0133121 A1 | 9/2002 | Bierman | |
| 2011/0301541 A1* | 12/2011 | White | A61M 25/0637 604/164.04 |
| 2013/0158506 A1 | 6/2013 | Harris et al. | |
| 2014/0296829 A1* | 10/2014 | White | A61M 25/02 604/508 |

FOREIGN PATENT DOCUMENTS

| | | |
|---|---|---|
| CN | 102892457 A | 1/2013 |
| CN | 203935281 U | 11/2014 |
| JP | S61-253073 A | 11/1986 |
| JP | H5-345032 A | 12/1993 |
| JP | H8-257129 A | 10/1996 |
| JP | 2004-528127 A | 9/2004 |
| JP | 2013-529116 A | 7/2013 |
| WO | WO 2011/146769 A2 | 11/2011 |

OTHER PUBLICATIONS

Office Action including Search Report on corresponding foreign application (CN Application No. 201680050987.5) from the National Intellectual Property Administration, P.R. China dated Mar. 4, 2020.
International Search Report & Written Opinion on corresponding PCT application (PCT/EP 2016/065490) from International Searching Authority (EPO) dated Oct. 12, 2016.
U.S. Appl. No. 13/111,716, filed May 19, 2011, 100 pages.
U.S. Appl. No. 61/407,777, filed Oct. 28, 2010, 64 pages.
Office Action on corresponding foreign application (JP Application No. 2017-568206 ) from the Japan Patent Office dated Jun. 23, 2020.
Office Action on corresponding foreign application (CN Application No. 201680050987.5) from the National Intellectual Property Administration, P. R. China, dated Nov. 17, 2020.
Final Office Action on corresponding foreign application (JP Application No. 2017-568206 ) from the Japan Patent Office dated Nov. 10, 2020.

* cited by examiner

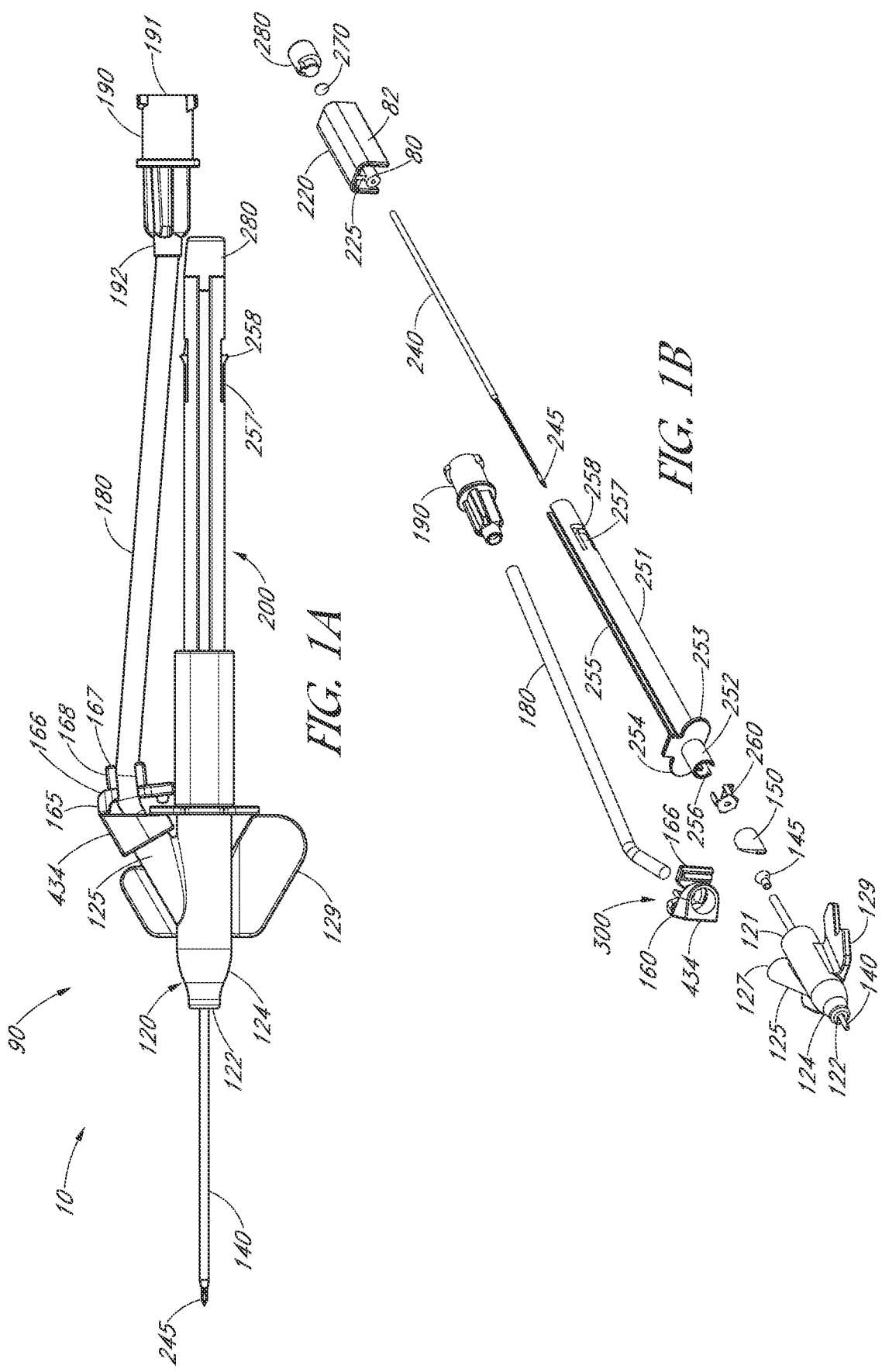

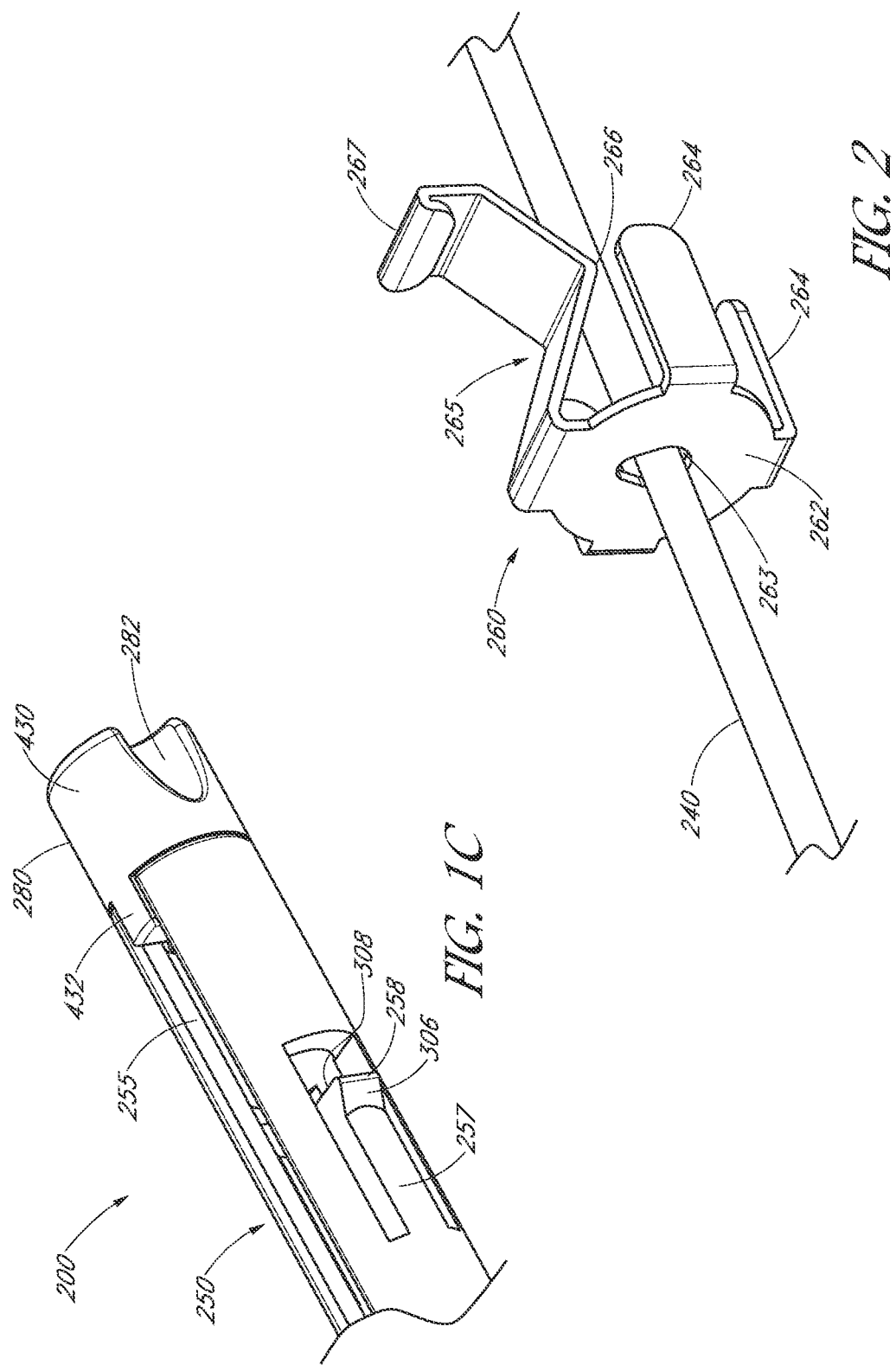

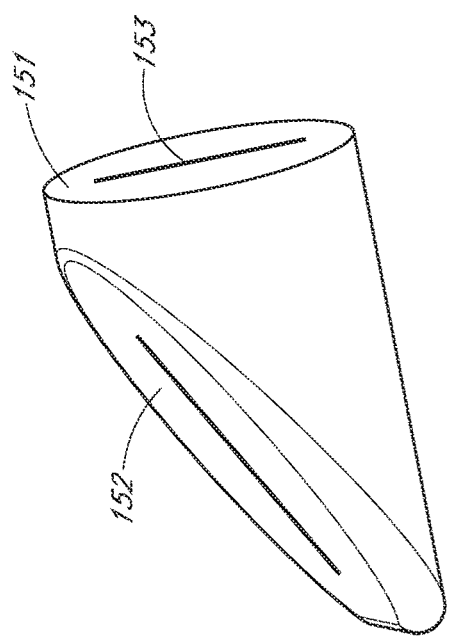
FIG. 4A
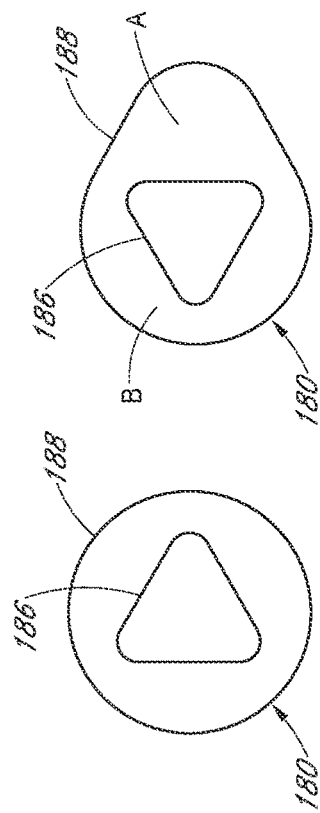
FIG. 5A
FIG. 5B
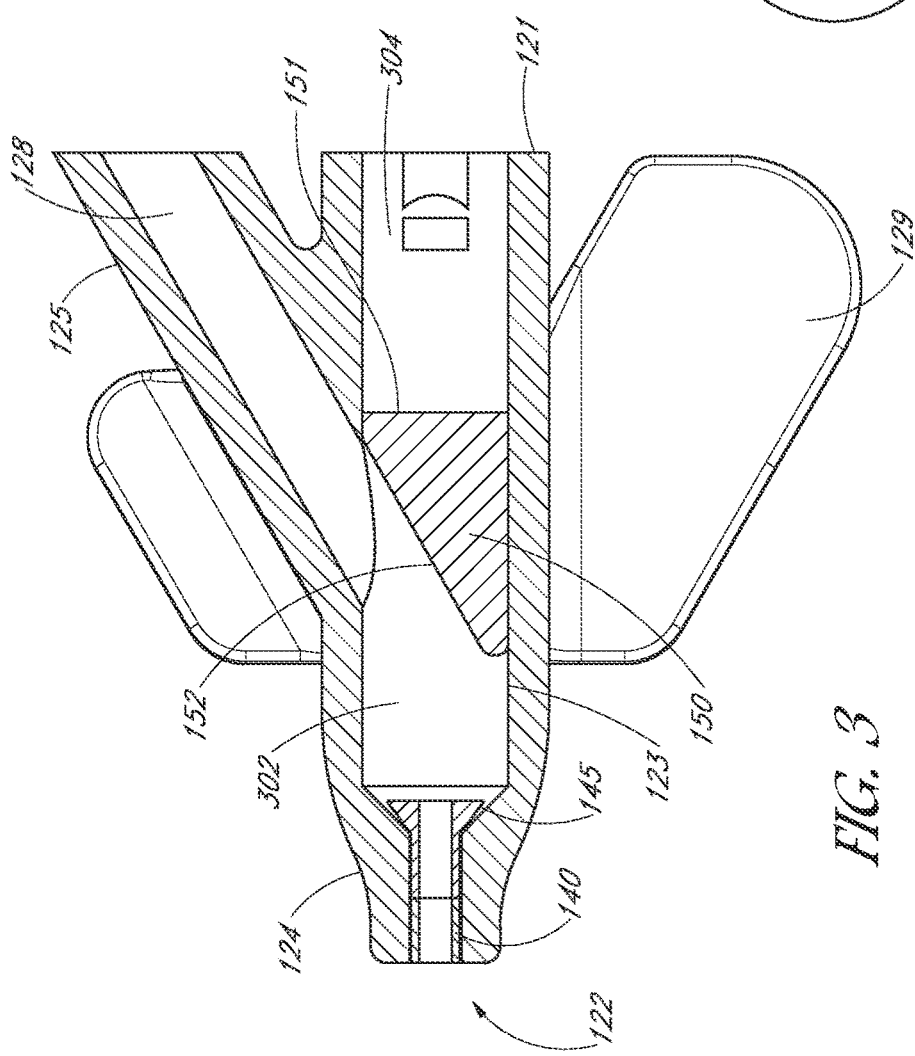
FIG. 3

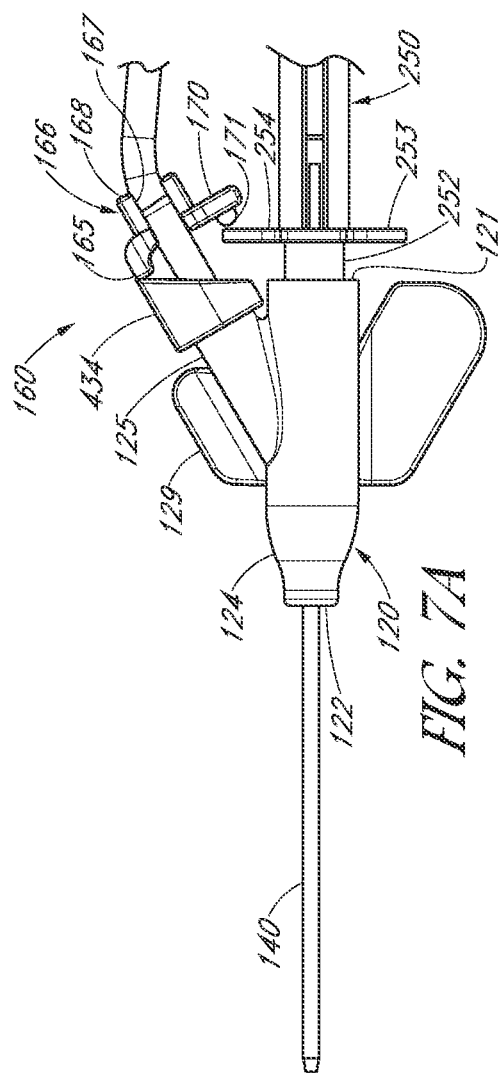
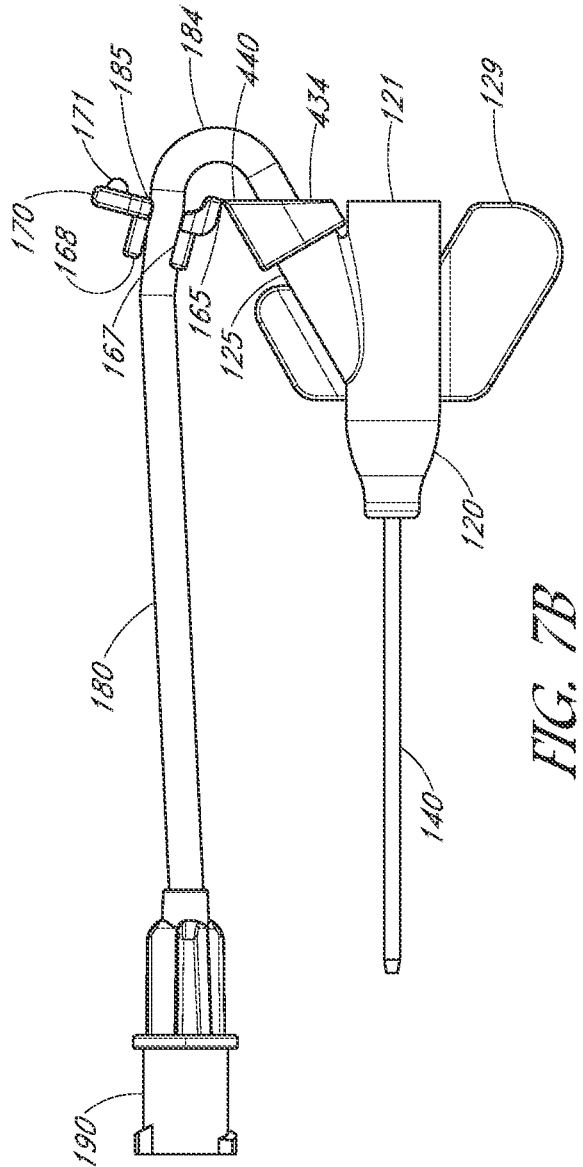

CATHETER DEVICES WITH INTEGRATED TUBING MANAGEMENT MECHANISM AND RELATED METHODS

FIELD OF ART

The disclosed invention generally relates to intravenous (IV) infusion devices, including IV and arterial catheter devices. In particular, catheter devices and related methods having tubing management systems are disclosed.

BACKGROUND

Needle devices are commonly used for a variety of infusion therapies, including infusing fluids into a patient, withdrawing blood from a patient, or monitoring various parameters of the patient's vascular system. After placement, a catheter tube connected to a catheter hub is typically connected to an adapter which then connects to an IV tubing. An IV fluid source can be connected to the catheter hub via the flexible IV tubing. Once connected, fluid from the IV source can begin flow into the patient through the tubing and the catheter. Conventionally speaking, the proximal end is the end closer to the practitioner and the distal end is the end away from the proximal end.

SUMMARY

Aspects of the present disclosure include catheter devices. The catheter devices described herein can be a catheter assembly. The catheter assembly can be an over the needle catheter or an IV catheter assembly.

The catheter device can comprise a catheter hub comprising a catheter hub body and a side port having a lumen and extending from the catheter hub body. The catheter hub body can have a proximal end a distal end, and an interior cavity.

The catheter device can further comprise a catheter tube attached to the distal end of the catheter hub body.

The catheter device can also comprise a septum located in the interior cavity of the catheter hub body between the distal end and the proximal end of the catheter hub body, thereby isolating a distal hub chamber distal of the septum from a proximal hub chamber proximal of the septum, the septum preventing fluid flow between the distal hub chamber and the proximal hub chamber. The septum can direct fluid flow between the distal hub chamber and the lumen of the side port.

The catheter device can further comprise a needle assembly.

The needle assembly can comprise a needle projecting through the septum and the catheter tube in a ready to use position. The needle can have a needle tip extending out a distal end of the catheter tube in the ready to use position, and a proximal end attached to a needle hub.

The catheter device can further comprise a flexible tubing having an end coupled to an opening of the side port, a connector coupled to another end of the flexible tubing, and a tubing management system configured to bend the flexible tubing. The tubing management system can comprise a clamp coupled to the catheter hub and receiving the flexible tubing therein.

The clamp can be a C-shaped clamp having an opening smaller than a cavity of the clamp. A width of the opening of the clamp can be less than a smallest width of the flexible tubing. The smallest width of the flexible tubing can be an outer diameter of the flexible tubing.

The flexible tubing can be a kink-resistant tube. The kink-resistant tube can have a circular or non-circular internal bore such as a triangular shaped cross-section. The kink-resistant tube can have a circular or non-circular outer circumference, such as cam shaped.

The tubing management system can further comprise a notch on the needle assembly to removably hold the flexible tubing in the ready to use position.

The needle assembly can further comprise a needle shield configured to secure the needle tip in the needle shield in a retracted position. The needle shield can comprise a flange, a proximal portion extending proximally of the flange, and a distal portion extending distally of the flange. The needle hub can abut against the flange in the ready to use position.

The needle shield can further comprise a spring clip located proximal of the septum to secure the needle assembly to the catheter hub. The spring can comprise a face having an aperture for the needle to pass therethrough, and a securing arm extending proximally from the face. The securing arm can comprise an elbow pressing against the needle in the ready to use position, and a tip coupled to the elbow and pressing against an interior surface of the proximal hub chamber.

A slot can extend from the flange to a proximal end of the proximal portion of the needle shield, and the needle hub has a tab for sliding proximally in the slot from the ready to use position to the retracted position.

A catch can be formed at the proximal portion of the needle shield to engage with and retain the needle hub in the retracted position.

A cap can be coupled to a proximal end of the proximal portion. The cap can have a notch to removably hold the flexible tubing in the ready to use position.

The needle assembly can further comprise a vent attached to the needle hub to allow gas to escape after a successful venipuncture.

The septum can form a seal with the interior cavity of the catheter hub body. The septum can be press fitted in the interior cavity of the catheter hub body. The septum can have an opening extending through a central portion of the septum.

A distal end of the septum can be shaped to smoothly direct fluid flow between the distal hub chamber and the proximal hub chamber. The distal end of the septum can be chamfered.

The needle can project through the opening of the septum in the ready to use position.

The connector can be a female Luer access connector.

The catheter hub can further comprise a pair of wing extending from opposite sides of the catheter hub body.

The tubing management system can further comprise a tube deflector comprising a deflector arm pivotably coupled to the side port from the ready to use position to an open position. The deflector arm can resist pivoting from the ready to use position to the open position until the deflector arm is pivoted beyond a threshold pivot point. The deflector arm can comprise the clamp.

The tube deflector can further comprise a fixed side attached to an open end of the side port with the deflector arm pivotably attached to the fixed side by a hinge. The fixed side can be attached to the open end of the side port by a mechanical snap fit, adhesive, or by ultrasonic welding.

The hinge can be a living hinge. The fixed side can comprise a collar, a collar hole defined through the collar, and the proximal end of the port can be received in the collar hole. The collar can have a chamfer at a proximal end of the collar substantially coplanar with the proximal end of the catheter hub body.

The needle assembly can engage the deflector arm of the tube deflector from the ready to use position past the threshold point to the open position during withdrawal of the needle assembly from the catheter hub.

The deflector arm can further comprise a flange with the clamp extending from the flange.

The needle assembly can press against the flange to pivot the deflector arm from the ready to use position past the threshold point to the open position during withdrawal of the needle assembly from the catheter hub.

A bumper can extend from the flange of the deflector arm of the tube deflector. The needle assembly can press against the bumper to pivot the deflector arm from the ready to use position past the threshold point to the open position during withdrawal of the needle assembly from the catheter hub.

The flexible tubing can slide along inside the clamp from the ready to use position to the open position. The flexible tubing can slide freely or with some resistance through the clamp. The clamp can have an inner diameter greater than or equal to an outer diameter of the flexible tubing.

The clamp can provide an elastic clamping force on the flexible tubing.

The clamp can extend from a distal portion of the catheter hub.

The tubing management system can further comprise a tubing slot at a side of the catheter hub body opposite the side port. The tubing slot can secure a portion of the flexible tubing. The flexible tubing can extend proximally from the side port and form a U-shaped bend to be secured in the tubing slot in an open position, and form another U-shaped bend from the tubing slot to the clamp and return proximally towards the needle assembly.

The flexible tubing can also be removably attached to a notch on the needle assembly.

Another aspect of the present disclosure includes a method for manufacturing the catheter device. The method can comprise attaching a catheter tube to a distal end of the catheter hub, said catheter hub comprising a catheter hub body and a side port extending from the catheter hub body, the catheter hub body comprising an interior cavity and an opening at a proximal end and a distal end, the side port having a lumen communicating with the distal end of the catheter hub body through the interior cavity.

The method can further comprise placing a septum in the interior cavity of the catheter hub body, said septum allowing fluid flow between the side port and the opening at the distal end of the catheter hub body, but preventing fluid flow between the distal end of the catheter hub body and the proximal end of the catheter hub body.

The method can also include attaching a tubing management system configured to bend a flexible tubing extending from the side port, the tubing management system comprising a clamp coupled to the catheter hub and receiving the flexible tubing therein to form a U-shaped bend.

The method can further comprise projecting a needle at the proximal end of the catheter hub body through the septum at the opening and through the catheter tube so that a needle tip of the needle extends distally of a distal end of the catheter tube in a ready to use position; said needle having a proximal end attached to a needle hub.

Yet another aspect of the present disclosure includes a method of using a catheter device comprising a catheter hub with a catheter tube, a needle attached to a needle hub, a septum located in an interior cavity of the catheter hub, and a tubing management system configured to bend a flexible tubing extending from the catheter hub, the tubing management system comprising a clamp coupled to the catheter hub and receiving the flexible tubing therein, said method comprising removing the needle and the needle hub from the catheter hub, the septum, and the catheter tube and forming a U-shaped bend with the flexible tubing engaged in the clamp.

The method can further comprise placing a male medical implement into a flexible tubing extending from a port of the catheter hub.

The method can further include infusing fluid from the male medical implement to the patient or withdrawing fluid from the patient to the male medical implement. The septum can allow fluid flow between the port and the opening at the distal end of the catheter hub body, but prevents fluid flow between the distal end of the catheter hub body and the proximal end of the catheter hub body.

A catheter device or assembly, such as an over-the-needle catheter assembly or an IV catheter assembly, can comprise a needle assembly, a catheter hub unit comprising a catheter hub having a catheter hub body and a side port extending from the catheter hub body, a catheter tube extending distally from the catheter hub body, a connector at an end of a flexible tubing, which is connected to the catheter hub, a septum located in an interior cavity of the catheter hub body, and a tubing management system for managing the flexible tubing.

A catheter device can comprise a needle assembly, a catheter hub unit comprising a catheter hub having a catheter hub body and a side port extending from the catheter hub body, a catheter tube extending distally from the catheter hub body, a connector connected to a flexible tubing, which is connected to the catheter hub, and a septum located in an interior cavity of the catheter hub body but having a different tubing management system.

A needle assembly in a ready to use position comprising a needle hub, a needle having a needle tip projecting distally from a nose section of the needle hub through a proximal end of the catheter hub body of the catheter hub, the septum, and in through the catheter hub and the catheter tube with the needle tip extending out a distal end of the catheter tube for accessing the vasculature of the patient.

The ready position can have the needle tip extending out a distal end of the catheter tube. The needle hub can have a cylindrical, rectangular, or any shape cross-section that can aid a user gripping the needle hub. Surface features, such as fins and bumps, may be added to further aid in the gripping. The needle hub can have a rectangular cross-section with rounded edges. The needle hub can include a flashback chamber and a proximal opening covered with a vent to allow air or gas to escape as blood flows into the needle and into the flashback chamber after a successful venipuncture. The vent can be part of a vent plug or a blood stopper.

The needle can be notched or non-notched, any acceptable gauge, and any acceptable length.

For a notched needle having an opening near the needle tip, indication of successful venipuncture can occur when the needle tip and the distal end of the catheter tube enter the vasculature and blood enters the needle lumen and out the notched opening of the needle and into the annular space between the catheter tube and the needle and into the catheter hub.

For a non-notched needle, blood can enter through the lumen of the needle and into the flashback chamber of the needle hub. Blood can also be drawn into a blood stopper connected to the proximal opening of the needle hub. Once successful venipuncture has occurred, the needle assembly can be detached and removed from the catheter hub.

The needle assembly can further comprise a needle shield to shield, guard, cover, or secure the needle tip of the needle when the needle hub is withdrawn proximally away from the catheter hub from the ready to use position to a retracted position.

The needle shield can comprise a flange, a hollow proximal portion extending proximally from the flange, and a hollow distal portion extending distally from the flange. The distal portion of the needle shield may be configured to extend into the interior cavity of the catheter hub body with the flange abutting against a proximal end edge of the catheter hub body in the ready to use position.

The proximal portion of the needle shield can be a hollow body having a slot extending axially along the lengthwise axis of the hollow body. For example, the slot of the proximal portion can extend from the flange to a proximal end edge of the proximal portion.

The distal portion can be a hollow body having a gap or a slot extending axially along the hollow body. In one example, the needle shield can include a proximal portion and a distal portion with each having a hollow cylindrical body and a lengthwise slot, wherein each portion has a C-shaped cross section due to the lengthwise slot. The two slots can be aligned or offset. The slot can vary in width and can be sized and shaped to allow a structure or feature to slide along the length of the respective slots.

The flange can have an area profile that is generally larger than the diameter or cross-sectional profile of the distal portion and the proximal portion. The flange can also have a larger profile than the proximal end of the catheter hub body so as to abut the proximal end or at least limit further insertion of the distal portion into the catheter hub in the catheter ready to use position.

The flange may or may not have flange extensions extending radially outwardly relatively to the lengthwise axis of the device to engage and activate the tubing mechanism. In some examples, the flange can have a shape of a two-leaf clover, a three-leaf clover, or a four-leaf clover. In other examples, the flange can be round, oval, elliptical, or polygonal in shape.

The length of the needle shield can be selected so that in the needle retracted position following venipuncture, the needle tip is recessed from the distal end edge of the distal portion.

After successful venipuncture, the needle hub is slidable axially along the slot of the proximal portion from the ready to use position in which the needle hub abuts against the flange of the needle shield or is in close proximity of the flange to a retracted or secured position in which the needle hub is substantially away from the flange. This movement of the needle hub relative to the needle shield has the effect of retracting the needle shaft and the needle tip into the needle shield.

In an example, a tab can be formed with the needle hub to slide inside the slot of the proximal portion of the needle shield to guide the needle hub from the ready to use position to the retracted position. For example, the tab can be incorporated to connect an elongated needle hub cylinder of the needle hub to an outer shroud. In some examples, there can be two or more aligned tabs, which may also be referred to as fins. Thus, the slot can confine the tab to limit rotational travel of the needle hub relative to the needle shield.

The slot can be closed off by a cap fixed at a proximal end of the proximal portion to prevent the tab of the needle hub from displacing proximally out of the slot. The cap can also incorporate other surface features to perform other functions, such as to temporarily secure the tubing and/or the connector.

In one example, when the needle hub is in the retracted position following use, the needle hub can be prevented from moving from the retracted position with the needle tip shielded or covered by the needle shield to re-expose the needle tip, such as to move the needle tip from the cover of the needle shield.

In an example, the limiting mechanism to prevent re-exposure of the needle tip can be a catch extending from a tab located near the end of the proximal portion of the needle shield. The tab can be formed with three continuous slots on the shield body to create a cantilever spring portion.

In an example, two or more combinations catch and tab can be incorporated on the needle shield. The catch can engage the needle hub in the retracted position to fixedly secure the needle hub to the needle shield.

In one example, as the needle hub slides proximally away from the catheter hub along the proximal portion of the needle shield, the shroud of the needle hub gradually presses or deflects the catch inwardly thereby elastically deflecting the tab from its original state.

Once the needle hub is in the retracted position and the needle tip is covered, the tab and the catch can elastically return back to its original state and engage a detent or shoulder on the needle hub to restrict distal movement of the needle hub relative to the needle shield.

The catch can have a tapered surface at a distal portion to allow the needle hub to gradually bias the catch and the tab inwardly towards the lengthwise axis.

The catch can also have a stepped surface at a proximal portion of the catch to prevent the needle hub from biasing the catch and the tab inwardly once the needle hub is in the retracted position, thus capturing the needle hub in the retracted position.

In one example, the needle hub, for example the shroud, completely passes over the catch and the catch engages an internal shoulder, such as a detent or a recessed groove formed with the shroud 82 of the needle hub, to maintain the needle hub in the retracted position.

In another example, the catch can engage with a slot or opening in the needle hub to maintain the needle hub in the retracted position.

The needle assembly or device can further comprise a spring clip for removably securing the needle shield to the catheter hub in the ready to use position and during retraction of the needle hub following successful venipuncture.

The spring clip can be located proximally of the septum and secured to the distal portion of the needle shield.

The spring clip can engage the catheter hub when the needle is in the ready to use position and can disengage from the catheter hub when the needle is in the retracted or secured position.

The spring clip can comprise a wall having an aperture and a securing arm extending proximally of the wall.

The spring clip may be rotated from its normal use position, which typically has the arm oriented towards the slot of the distal portion of the shield so that the free end of the arm can contact the interior cavity of the catheter hub through the slot.

In an example, the spring clip can have a wall having a proximally facing wall surface and a distally facing wall surface. The wall can be generally circular or round and can include a circular or non-circular aperture for the needle to extend therethrough in the ready to use position.

One or more supports can extend in a proximal direction from the wall. The supports are configured for attaching to the needle shield, such as to the distal portion of the shield. The attachment between the supports and the distal portion can be by mechanical means, such as by interference or spring load, by welding, by snap fit, or by adhesive. For example, the one or more supports can be sleeved to an inner surface or outer surface of the distal portion of the needle shield and form a tight interference fit to fix the spring clip to the distal portion.

The supports of the spring clip and therefore the spring clip can be fixedly secured to the needle shield in both the ready position and the needle retracted position or secured position.

The spring clip can further comprise a securing arm having an elbow extending from the wall, and a tip at a free end of the arm. The elbow can be L-shaped, can have an acute angle or an obtuse angle, and is configured to contact with and be biased outwardly by a side of the needle in the ready to use position.

The biasing by the needle on the elbow can cause the tip at the free end of the arm to project through the slot of the distal portion of the shield to press against and removably engage with the interior cavity of the catheter hub, such as to the proximal hub chamber of the catheter hub body. This allows the spring clip to secure the needle shield, to which the spring clip is fixedly secured, to the catheter hub body until the biasing is removed, at which time the needle shield can separate from the catheter hub.

In some examples, the tip has a shaped lip for engaging a corresponding notch or detent in the interior of the catheter hub body.

In an example, the arm has a length and each support has a length. The supports can also be considered or called arms extending from the wall.

In one embodiment, the length of the arm is longer than the length of each support.

In another embodiment, the length of each support is longer than the length of the arm.

In still other examples, the arm can be longer than one support but shorter than a second or different support.

The spring clip can comprise a wall having a perimeter defining an opening, said wall having a distally facing wall surface and a proximally facing wall surface, and wherein a plurality of arms extend in a proximal direction.

The plurality of arms can have different lengths. The spring clip can be without any distally extending arms or arms that extend in the distal direction.

In other examples, a partially enclosed structure having a shape of the interior of the distal portion is incorporated with the spring clip and the supports are omitted. The arm can be located in the gap or space of the partially enclosed structure and the partially enclosed structure can be fixedly secured to the distal portion.

In one embodiment, the spring clip comprises a wall having an opening and two or more arms extending proximally from the proximally facing wall surface of the wall. In an example, the spring clip can comprise three or more arms extending in the proximal direction from the wall and wherein at least one of the arms is configured to contact and be biased by a side of the needle in the ready to use position to press against an interior of a catheter hub body.

The arm being biased can project through a gap of the needle shield to press against the interior of the catheter hub body.

In a ready to use position, the needle projects through the septum and through the spring clip and biases the elbow of the spring clip to bias the arm outwardly so that the tip of the spring clip, which is at a free end of the arm, engages the catheter hub to secure the needle shield to the catheter hub.

A catheter device can comprise a spring clip comprising a wall having a plurality of proximally extending arms and wherein the spring clip is secured to a needle shield and is biased by a needle into removable engagement with a catheter hub in a ready to use position.

In an example, at least one of the arms is fixedly secured to a distal portion of the needle shield.

In an example, one of the arms can be biased by the needle so that a free end of the biased arm projects through a slot on the needle shield to removably engage the catheter hub.

In a ready to use position and in an example of the present disclosure, the needle presses against the elbow to deflect it outwardly, which causes the tip at the free end of the spring clip to engage or press against a surface or engagement mechanism in the interior cavity of the catheter hub body. When the needle hub and needle are retracted proximally from the catheter hub following successful venipuncture, the needle is moved proximally until the needle tip moves proximal of the elbow, which then frees the arm from the bias of the needle. This allows the arm to move radially inwardly and the tip at the free end of the arm to space from the interior surface of the catheter hub. At this point, the elbow elastically returns inwardly to its normal unbiased position or state, thereby disengaging the tip of the arm from the surface of the interior cavity of the catheter hub body. With the tip of the arm spaced from the interior surface of the catheter hub, the needle shield no longer attaches to the catheter hub body and the combination needle assembly and needle shield can now detach or separate from the catheter hub.

A catheter hub can comprise a hub body, a side port extending from the catheter hub body, and a pair of wings extending from opposite sides of the catheter hub body to provide additional surface area beyond just the area of the catheter hub to secure the catheter hub to the patient.

The wings can be attached to the catheter hub body by mechanical means, such as by snap fit, welding, or by fasteners, or be integrally molded to the catheter hub body. In the illustrated embodiment, the wings can elastically deform and integrally formed and extend radially outwardly from a bottom region of the catheter hub body. The wings can have any number of shapes and can serve as a grip for the user to hold when using the catheter device 10. The side port has a lumen in fluid communication with the interior cavity of the catheter hub body. The proximal end of the catheter hub body can have a female luer connector with a female luer taper and can include external threads to matingly receive a threaded male Luer.

The external threads may be configured for engagement with the distal portion of the needle shield.

The side port can be configured for delivering fluids, such as medicament, IV solution, or other fluids, to the patient rather than through the proximal end of the catheter hub body, which can be sealed off by the septum located inside the catheter hub.

The septum can be positioned in the interior cavity of the catheter hub body between the distal end and the proximal end of the catheter hub body to isolate a distal hub chamber from a proximal hub chamber when the septum is closed, such as after the needle is removed therefrom.

The septum can prevent fluid flow between the distal hub chamber and the proximal hub chamber and contain or limit fluid flow to the area between the distal hub chamber and the lumen of the side port.

The septum can be made of a biocompatible elastomeric material such as a silicone material.

The septum forms a seal with the interior wall surface of the interior cavity of the catheter hub body. In one example, the septum can be wedged or press fitted in the interior cavity of the catheter hub body, thereby forming the seal between the septum, such as between the exterior wall surfaces of the septum, and the interior wall surfaces of the interior cavity.

In another example, the septum can be pushed against and engage between one or more circumferential projections when assembling the septum to the interior cavity of the catheter hub body.

The septum can also be secured to the interior cavity of the catheter hub by a securing mechanism, such as an additional holder or retaining ring ultrasonically welded to the catheter hub, or by using adhesive.

A septum can be cylindrical at a proximal end and then slanted at a distal end, opposite the proximal end. The slanted surface can match the angle of the side port. The slant can taper into a small profile near a distal end edge of the septum.

A slit or a slot can extend from a wall on the proximal portion to the distal portion of the septum and through the slanted surface. The slit can expand or open to allow the needle to project through the slit of the septum in the ready to use position. Following use when the needle is retracted proximally out the septum, the slit seals or closes upon itself to prevent fluid from flowing therethrough. The slit can be formed from a line cut through the length of the septum.

In other examples, the septum has a slanted distal wall and a hollow bore with a proximal wall having one or more flaps defined by one or more slits formed on the proximal wall. In an example, three slits intersecting at a point forming three flaps are utilized with higher or lower number of slits contemplated. The slits can form a seal around a shaft of the needle.

After successful venipuncture, the needle is retracted proximally out the septum. As the needle slides out the septum, the flaps or portion of the septum surrounding the opening where the needle just vacated can wipe the blood off the surface of the shaft of the needle. After the needle is removed from the bore and the proximal wall with the flaps of the septum, a seal is formed at the slits to prevent blood from passing through the opening. That is, as the needle is removed from the septum, the septum can form a seal to prevent fluid passing through the septum between the distal hub chamber and the proximal hub chamber after the needle is withdrawn.

In another example, the septum does not have any opening, bore or slit, just a solid core. But because the septum can be made from an elastic material, such as silicone, rubber or other elastomeric material, it acts as a plug that can be pierced by the needle. The plug can seal upon itself upon retraction of the needle thereby preventing fluid from passing through the septum.

In another example, the septum can have a cavity that can trap fluid or house a fluid absorbent material therein. The cavity can extend to one end of the septum, such as distal of the proximal wall, or be confined between opposite ends of the septum. The cavity can be cylindrical or any other shape.

The distal end of the septum can be shaped to smoothly direct fluid flow between the distal hub chamber and the lumen of the side port after the needle is removed from the septum. For example, the distal end of the septum can be chamfered or curved so that the directed fluid can flow in either direction between the catheter tube and the flexible tubing attached to the side port.

In one example, a septum may be a split septum having a split extending partially along a length of the septum. The septum can be split entirely into two or more equal or unequal portions from a first end of the septum to a second end of the septum, which is a base portion without a split forming through the outer circumference.

The first end with the split can form a first end portion having a plurality of legs extending from the base portion. The legs can have equal or different sizes, such as different thicknesses formed by providing the split off-center.

At the end wall of the base portion, a slit can be provided. The slit at the base portion communicates with the split on the first end.

Interiorly of the septum, a recess is formed into each of the two legs so that when the two legs contact one another, the two recessed sections form a cavity within the septum. The cavity can be generally cylindrical in shape and bounded at two ends by a septum wall section having a slit, or a slit that is part of a split. In other examples, the cavity can be other than cylindrical in shape.

The slit at the first end can be formed completely across a diameter of the septum wall section. In one example, the slit at the second end or base portion is not formed completely across a diameter of the septum wall section of the base portion.

In use, the cavity of the septum can be configured to trap fluid or house a fluid absorbent material to absorb fluid, such as blood, that may flow around an exterior of the needle shaft, such as during secondary flashback.

When the split septum is placed inside a catheter hub body, the split septum can form a seal with the interior surfaces of the interior cavity of the catheter hub body, which imparts a radial compressive force on the split septum to close the slit at the base portion and the split at the first end.

A needle can project through the septum wall section with the slit at the second end, the cavity, and the septum wall section of the first end with the split. During retraction of the needle following successful venipuncture, any blood on the outside of the needle can be wiped by the two septum wall sections of the septum and be trapped or confined to the cavity.

In an example, the septum can comprise two septum sections or septum pieces arranged serially in the interior cavity of a catheter hub body. The two septum pieces can be identical or different from one another and can contact or be spaced apart from one another.

In one example, each septum piece comprises a body having a cylindrical contour and two ends and wherein each end has a concave portion. In an example, the concave portion is formed by a frustoconical shape void, a spherical shape void, or other surface sections forming a concave surface. The concave portion at each of the two ends of the septum piece can have a same or different depth and shape.

In an alternative embodiment, the septum piece can have one concave portion on one end and no concave portion at the other end. In one example, when two septum pieces are arranged serially in the interior cavity of the catheter hub body, a cavity is formed by two adjacent concave portions of two adjacent septum pieces.

A seal can be formed between the exterior of each of the two septum pieces and the interior surface of the interior cavity of the catheter body, such as by sizing the exterior dimensions of the septum pieces to be slightly larger than the interior dimension of the catheter body to create a compressive fit between the two.

A slit can extend through the body of the two septum pieces to facilitate insertion of the needle through the septum. Upon removal of the needle, the inward compression on the septum pieces by the catheter hub can cause the slits to automatically close. Fluid on the outside of the needle, such as blood from secondary flashback, can be wiped by one or both slits and retained within the cavity during retraction of the needle following successful venipuncture.

In one embodiment, the septum includes two septum pieces and a sleeve sandwiched between the two septum pieces. Each septum piece of can resemble a cap, which is understood to include a wall and a cylindrical skirt extending from the wall. The wall can further include a perimeter defining an opening that is sized and shaped to accommodate a needle shaft, in a size-on-size fit, loose fit, or interference fit.

The interior of the cylindrical skirt of the septum pieces can be sized and shaped to accept the sleeve when the septum pieces are arranged serially inside the interior cavity of the catheter hub body. In an example, when so arranged in the interior cavity, the two skirts contact one another at the axial end of each.

In one embodiment, the two skirts do not contact one another and a gap is provided between the two, which exposes the sleeve at an area between the two cylindrical skirts. The sleeve can be cylindrical in configuration and can include a bore or lumen and be made from a similar material or different material than the septum pieces. For example, the sleeve can be made from a material that has hydrophilic properties or liquid absorbing properties.

The bore of the sleeve may also be provided with a coagulating agent. Following successful venipuncture, the needle can be retracted from the septum. During the retraction step, blood on the exterior of the needle can be wiped by one or both openings on the two walls and be captured or retained inside the bore of the sleeve.

In one example, a septum may be positioned inside the interior cavity of a catheter hub body. The septum may embody a multi-piece septum structure. The septum can include two identical septum bodies. Each septum body can have a septum housing element and a septum sealing element received in an interior cavity of the septum housing element. Together, the combination septum housing element and septum sealing element can form a septum body.

A septum housing element can include a tapered internal surface for receiving a correspondingly shaped septum sealing element. In an example, the internal surface embodies an hourglass-shaped chamber. The taper in the chamber can form a tight fit with the septum sealing element, similar to a size-on-size fit, which helps to reduce relative movement, such as translational movement, between the septum sealing element and the septum housing element.

The septum sealing element can include first and second flanges or shoulders and the septum housing element can include first and second undercuts formed in the chamber for accepting the flanges or shoulders.

A septum housing element can include an external annular flange or other protrusion to press into the internal cavity of the catheter hub body. The arrangement between the septum housing element and the catheter hub body can help to reduce translational movement between the two.

The two septum bodies can be arranged back to back so that they contact one another at an end inside the catheter hub body. In some examples, the two may be coupled together either before or after insertion into the catheter hub body through interference fit, ultrasonic welding, epoxy or adhesive, threads, and/or any suitable coupling mechanism. The septum housing element can incorporate weld beads so that the two septum housing elements can be welded together end-to-end prior to insertion into the catheter hub.

Each septum sealing element can include a cavity that extends inward from an open end opposite a closed end such that when the two septum bodies are assembled in the catheter hub body, the two open ends of the septum sealing element from each septum body can face or aligned to abut against each other. In this manner, the two cavities can form an enclosed septum cavity between two closed ends of the septum sealing elements.

A path, such as a slit or an opening, can extend through the septum sealing element of each septum body. A distal end of a septum can be chamfered or curved so that the directed fluid flow in either direction between the catheter tube and the flexible tubing can be made relatively smoother.

A catheter tube can extend distally from the distal end of the catheter hub body. A proximal end of the catheter tube can be attached to the distal end of the catheter hub by a bushing. The needle can project through the catheter tube and the needle tip can extend out a distal end of the catheter tube in the ready to use position.

The distal end of the catheter tube can taper inwardly or have a smaller inner diameter than the rest of the catheter tube, and smaller than the outside diameter of the needle shaft, to form a seal between the distal end and the shaft of the needle.

After successful venipuncture and as the needle is retracted proximally from the catheter tube, blood can flow through the catheter tube around the outside of the needle and into the distal hub chamber, which is in fluid communication with the flexible tubing through the lumen of the side port.

In an example, the flexible tubing has one of its ends connected to the side port. The other end of the flexible tubing can couple to a connector to deliver or withdraw fluid between the patient and the connector. Typically the longer the flexible tubing, the greater is the freedom in positioning and orienting the connector and preventing accidental pullouts.

The flexible tubing can be a traditional tubing section or can be a kink-resistant tubing to avoid restricting fluid flow through the flexible tubing and give the user or practitioner more freedom to route the flexible tubing in various ways, such as to bend or to manipulate the tubing, to accommodate placement of the connector at any number of locations on or about the patient during use. In an example, the flexible tubing can be made kink-resistant by having a non-circular tubing bore.

In an example, the non-circular tubing bore can have a triangular shaped cross-section. The apex of the three corners of the triangular bore can be pointed or radiused. In other examples, the non-circular tubing bore can have a polygon shape, such as a pentagon or a heptagon.

The non-circular tubing bore can allow the flexible tubing to curve sharply without kinking. The flexible tubing can also be made kink-resistant by having a non-circular outer circumference, with or without a non-circular tubing bore. In an example, the tubing is cam shaped or teardrop shaped with a non-circular triangular tubing bore that can instead be practiced with a traditional circular bore. In this example, the tubing material volume a first location has a smaller radii of curvature along an outer contour and has a greater material volume than the tubing section at a second location, which has a larger radii or curvature along an outer contour. In one example, the greater material volume at tubing the first location can be added onto a normal round tubing outer contour. An external force can be applied to the kink-resistant tubing and bending the flexible tubing to form a J-loop bend or bending the kink-resistant tubing in various other ways to position the connector for use with minimal risk of completely blocking fluid flow due to tubing kinking. After the external force applied to the flexible tubing is removed, the flexible tubing can recover to its original shape or at least restore much of its original shape.

The connector can have a distal end coupled to the flexible tubing and a proximal end configured to receive an IV connector or other fluid connection devices, such as a syringe tip or an IV adaptor, for fluid delivery, such as for delivery of medicament, IV solution, or other fluids, through the catheter hub body.

In one example, the proximal end of the connector can be a female Luer connector with optional external threads to form a threaded female Luer. The female Luer connector is configured to matingly receive a male Luer connector, such as an IV line, a Luer access connector, a syringe tip, a vent plug, other known connectors or future-developed IV devices. Each of these components can be sized and shaped in conformity with at least some of the International Standards Organization (ISO) standards for female and male Luer connections under current or future standards.

A tubing management system can be configured to route the flexible tubing to a predetermined or desired position for line connection, maximize the length of flexible tubing available for line connection, minimize tube kinks, and/or provide a J-loop bend to prevent accidental pull outs, as will be discussed below.

A first exemplary tubing management system can be coupled to the catheter hub, such as formed with or attached to the catheter hub body, and comprises a clamp. In other examples, the tubing management system can be molded as a unitary structure or be fixedly attached to the catheter hub. The flexible tubing is received in the clamp and held to the catheter hub body by the clamp. In one example, the clamp can be a C-shaped clamp having an opening with a width sized and shaped to receive the flexible tube and a cavity for holding the flexible tube.

The cavity can be smaller than a smallest width of the flexible tube so that the flexible tube can be squeezed when pushed through the opening and into the cavity of the clamp and be retained in the cavity. The width of the opening of the clamp may be the same or smaller than the smallest width of the flexible tubing to prevent the flexible tubing from slipping out of the cavity after the flexible tubing has been secured in the clamp. For example, if the flexible tubing has a noncircular outer circumference, the smallest width of the flexible tubing can be larger than the width of the opening to prevent the flexible tubing from displacing from the cavity through the opening.

In some examples, the opening of the clamp may have a lip for limiting the flexible tubing from slipping out of the opening but the relative sliding movement between the flexible tubing and the interior wall surface of the clamp is possible.

A notch on the shield of the needle assembly can be utilized to removably hold a portion of the flexible tubing remote from the clamp, such as near the connector in the ready to use position. The notch can be located on a cap attached to the proximal end of the needle shield.

The cap can have a cylindrical shaped body with the notch formed therein and a rectangular projection extending out a distal end to frictionally engage the shield at the slot. Optionally, detents, adhesive, or other attachments means may be incorporated for attaching the cap to the shield.

In other examples, the notch or other holding structures, such as a clamp, can be incorporated directly with the shield, such as being co-molded, over-molded, or unitarily formed with the shield. A tubing section adjacent the connector, the connector, or both can be supported by the notch to support the weight of the connector as the catheter device is inserted into the patient to access the patient's vasculature. The notch can also effectively support the connector when the catheter device is packaged neatly inside a blister pack or other packaging material. The notch also keeps the connector and the flexible tubing from hindering or obstructing the user during use on a patient.

In some examples, the tubing management system can comprises a tube deflector comprising a base and a deflector arm coupled to the base by a hinge. The clamp may be located on or be part of the tube deflector.

In some examples, the tube deflector is integrated with the catheter hub and the base is omitted. The base can comprise a collar for coupling to a side port of the catheter hub body, such as for positioning over the side port and receiving the side port inside the hole.

The deflector arm of the tube deflector can be rotatable about the hinge from a ready to use position to an open position shown in which the deflector arm swinging away from the base. In the ready to use position, the flexible tubing can be secured to the side port and can extends through and be held by the clamp.

The flexible tubing can extend in the proximal direction from the side port and can be connected to the connector. In this position, the length of the flexible tubing, in one example, should be long enough to extend from the side port to the notch.

After successful venipuncture, the deflector arm of the tube deflector can be pivoted with respect to the base about the hinge, such as by gripping the connector and moving the connector so that the flexible tubing causes the deflector arm to rotate. A user can also grab the deflector arm directly to rotate the deflector arm about the hinge.

In some examples, the deflector arm is automatically rotated by the proximal movement of the needle assembly. Movement of the deflector arm can cause the flexible tubing to form a bend as the deflector arm pivots from the ready to use to the open position shown. In this position, a J-loop or U-shaped bend is formed.

During the rotation of the deflector arm, the flexible tubing can slide inside the internal cavity of the clamp while the clamp biases and bends the flexible tubing to form the U-shaped bend or J-loop.

The clamp can surround, loosely hold, or grip the flexible tubing. The clamp and the flexible tubing can slide freely relative to one another or there can be some resistance as the deflector arm of the tube deflector rotates from the ready to use position to the open position and moves relative to the flexible tubing.

In one example, the interior cavity of the clamp can be slightly larger than the flexible tubing so that the flexible tubing can slide freely relative to the clamp.

In another example, the interior cavity of the clamp can be substantially equal to the flexible tubing to provide some resistance to the flexible tubing when sliding inside the interior cavity of the clamp.

In yet another example, the interior cavity can be slightly smaller than the outside diameter of the flexible tubing to produce a clamping force against the flexible tubing. For example, the clamp can have an inner diameter greater than an outer diameter or size of the flexible tubing.

In another example, the clamp can have an inner diameter smaller than or equal to an outer diameter or size of the flexible tubing, such that the clamp provides an elastic clamping force on the flexible tubing. However, for this example, the clamp should be flexible enough to expand such that the flexible tubing is slidable within the clamp.

The length of the clamp measured between two open ends can also affect the resistance of the deflector arm to pivot because the relatively longer length can lead to a larger frictional surface area and/or can prevent the flexible tubing from bending inside the clamp. A relatively shorter length of the clamp measured between the two open ends may produce less resistance than a relatively longer clamp.

The opening of the clamp can be selected to control the relative ease or complexity of installation of the tube inside the clamp. For example, a relatively large opening allows the flexible tubing to slide freely inside the interior cavity of the clamp during assembly prior to use of the catheter device while a relatively smaller opening will require deflecting or compressing the flexible tubing, at least partially, to enable insertion into the interior cavity.

The opening can also permit the clamp to expand elastically to accommodate the flexible tubing as the clamp pivots about the side port. For example, the clamp can be relatively thin and/or made from a flexible material so that when deflected, the clamp will give to enable flexing. When the deflector arm of the tube deflector rotates towards the open position, the flexible tubing can slide along the clamp and form the rounded bend, such as the U-shaped bend or J-loop bend.

The deflector arm of the tube deflector can further comprise a flange. The C-shape body of the clamp can extend from the flange along one or both sides of the flange. The C-shape body extends in the proximal direction only out the proximally facing surface of the flange when the flange is in the ready to use position. Generally, the clamp can be aligned such that the axis of the clamp is orthogonal to the axis of pivot to minimize resistance to rotation about the pivot or hinge.

A bumper can extend from the flange of the deflector arm of the tube deflector in a direction towards the base in the closed or ready to use position. The bumper can be sized to increase or decrease the gap between the surface of the flange and the flange extension on the needle shield, as further discussed below.

The flange and the bumper can present a gripping area for a user to grasp the deflector arm and pivot the deflector arm from the ready to use position to the open position.

Alternatively, a structure on the needle assembly can abut and push against the flange, the bumper, or both to passively move the deflector arm to the open position.

The shield extension of the shield flange on the shield can overlap with the flange and/or the bumper in a radial direction relative to the lengthwise axis of the catheter assembly or device. In other words, the flange, the bumper, or both stand along the pathway of the shield extension of the needle shield. For example, when the needle assembly is retracted from the catheter hub following successful venipuncture, the shield extension can push against the bumper in the proximal direction, which causes the deflector arm to pivot from the ready to use position to just past a threshold point of the hinge, which can be a living hinge.

This threshold point can be defined by a point in which the stress/strain of the hinge causes the hinge to change its position and continue its rotation to the open position. The threshold pivot point can prevent the deflector arm from prematurely or unintentionally pivoting to the open position until a sufficient force physically initiates the pivot of the deflector arm past a certain distance.

In an example, as the needle and the needle hub are retracted proximally away from the catheter hub following use, the shield flange will move proximally away from the catheter hub after the spring clip disengages from the catheter hub, as previously described. As the shield flange moves proximally, the shield extension presses against the flange and/or the bumper and the deflector arm will begin to pivot. As the needle assembly continues to be withdrawn in the proximal direction, the shield extension continues to push against the deflector arm of the tube deflector while the clamp and the flexible tubing slide relative to one another and forces the flexible tubing to bend to form a J-shaped loop.

In an example, once the pivot point threshold is reached, the tube deflector swings automatically completely to the open position. That is, the deflector arm can swing to the open position without additional external force and the deflector arm can therefore open passively without additional external force.

In an example, the hinge of deflector arm, once the pivot threshold is reached, can overcome the resistance between the clamp and the flexible tubing, as well as the force required to bend the flexible tubing, to swing the deflector arm to the open position. In an example, a passive tubing management system can automatically orientate the tubing and forms a J-loop in the flexible tubing upon retraction of the needle hub from the catheter hub following successful venipuncture.

A structure on the needle assembly can initiate a pivot of the deflector arm during normal retraction of the needle assembly following successful venipuncture. Once a deflector arm pivots a certain amount beyond the pivot threshold of a hinge, the stress/strain on the hinge can automatically pivot the remaining rotational movement to cause a J-loop to form in the flexible tubing and the flexible tubing to change its orientation.

The needle assembly can be completely detached from the catheter hub with the tube deflector rotated to the open position until forcibly returned to the closed or ready to use position, such as by hand. By orienting the end of the flexible tubing with the connector in the same orientation as the insertion direction of the catheter tube, the J-loop bend of the flexible tubing can reduce the probability of accidental pullout of the flexible tubing from the catheter hub or the catheter tube from the patient.

In one example, a catheter device comprises a needle shield that does not have a shield flange or a shield extension. Thus, upon retraction of the needle assembly, the deflector arm on the tubing management system will not automatically rotate by the needle assembly to form a J-loop in the flexible tubing. Instead, a separate external force apart from simply retracting the needle assembly in the proximal direction is needed to pivot the deflector arm.

In an example, the external force is digital pressure or force applied to the deflector arm to rotate the arm about the hinge. Alternatively, a user can grip the connector, the tube, or both to rotate the deflector arm.

The tubing management system can be an active system requiring a separate force other than the retraction force of the needle assembly to remove the needle hub and the needle in the proximal direction to manually swing the deflector arm of the tube deflector from the closed or ready to use position to the open position prior to, during, or after the needle hub and the needle are withdrawn from the catheter hub.

In an example, as the deflector arm of the tube deflector is pulled or pushed by a user against the flange or bumper, the flexible tubing slides relative to the clamp of the deflector arm and begins to bend. Once the pivot point threshold of the hinge is reached, the deflector arm of the tube deflector swings to the open position.

The needle and needle hub can be completely detached from the catheter hub before, during, or after the tube deflector is in the open position. The tube deflector can remain in the open position until the deflector arm is forcibly returned back to the closed position.

Whether or not the needle assembly has a shield extension, the deflector arm can be pivoted manually or passively from the ready to use position past the threshold point to the open position before, during, or after withdrawal of the needle assembly from the catheter hub.

The tubing management system can comprise a base configured to attach to an open end of the side port. The base can comprise a collar having a wall structure defining a hole extending through the collar. The open end of the side port can be pressed inside the hole of the collar by interference fit, or attached by mechanical snap fit, adhesive, ultrasonic welding, or other attachment means.

The collar can have a chamfer at a proximal end, which can have an angle relative to the opposed end face of the collar so that the surface of the chamfer is substantially co-planar to the proximal end of the catheter hub body. This in turn allows the flange of the needle shield to sit flush against the proximal end of the catheter hub body.

In an alternative embodiment, the catheter device can be an over-the-needle catheter assembly or an IV catheter assembly comprising a needle assembly, a catheter hub having a catheter hub body and a side port extending from the catheter hub body, a catheter tube extending distally from the catheter hub body, a connector, a flexible tubing connected between the connector and the catheter hub, a septum located in an interior cavity of the catheter hub body similar to other embodiments discussed elsewhere herein, and a tubing management system for managing the flexible tubing, as further discussed below.

The tubing management system can comprise a tubing slot on a side of the catheter hub body opposite the location of the side port. The tubing slot can secure a portion of the flexible tubing in both the ready to use position and the open position.

The tubing slot can be separately formed and subsequently attached to the side of the catheter hub body or can be a groove or slot formed in the side of the catheter hub body opposite the side of the side port, such as by molding.

The tubing slot can be configured to hold the flexible tubing in place thereby forming a U-shaped or J-loop bend between the tubing slot and the proximal end of the side port where the tubing is attached in both the ready to use position and the open position.

In one example, the tubing slot can have a cavity sized smaller than a size of the flexible tubing to hold the flexible tubing in place, under a slight interference fit.

In another example, the tubing slot can have an opening smaller than a size of the flexible tubing but the cavity can be the same, smaller, or larger in size so that the flexible tubing can be squeezed through the opening and into the cavity of the tubing slot.

In some examples, a first free end of tubing is attached to the side port. The tubing then forms a first U-shape around a proximal side catheter hub body where it passes through the tubing slot and then extends toward the distal end of the catheter hub body and through the clamp and then back towards the proximal end of the catheter assembly forming a second U-shape bend, where it then terminates with the connector.

A cap with a notch, may be provided at the proximal end of the needle shield to support the tubing and/or the connector. The clamp can be separately formed and subsequently attached to the catheter hub or unitarily formed to a distal portion of the catheter hub.

The clamp may be configured to temporarily hold the flexible tubing in the ready to use position with the connector adjacent the proximal end of the needle shield. In one example, the flexible tubing can be slightly compressed in an interior cavity of the clamp to hold the flexible tubing in place.

In another example, the clamp can have an opening slightly smaller than a size of the flexible tubing so that the flexible tubing can be squeezed through the opening and secured inside the interior cavity of the clamp.

After successful venipuncture, the needle and the needle hub can be retracted proximally away from the catheter hub. The flexible tubing and/or the connector attached to the tubing can be removed from the notch on the cap to move to a used position.

The tubing and the connector can be swung in the distal direction from the proximal position to detach from the clamp and move to the open position. In the tubing open position, the tubing slot continues to hold part of the tubing to maintain the first U-shape in the tubing. The connector at the second end of the flexible tubing can be connected to a male Luer connector or other mating connector.

In alternative embodiments, rather than a needle shield, the catheter assembly can incorporate a needle tip protector. The needle tip protector can be positioned inside the catheter hub where a spring clip sits and separates from the catheter hub upon retraction of the needle following use.

BRIEF DESCRIPTION OF THE DRAWINGS

These and other features and advantages of the present devices, systems, and methods will become appreciated as the same becomes better understood with reference to the specification, claims and appended drawings wherein:

FIG. 1A is an assembled top view of an embodiment of a catheter device of the present disclosure;

FIG. 1B is an exploded perspective view of the catheter device of FIG. 1A;

FIG. 1C is a partial assembled isometric view of the needle shield of FIG. 1A, showing a notch on a needle assembly;

FIG. 2 is an isometric view of a needle engaged with a spring clip of the needle assembly of the catheter device;

FIG. 3 is a partial cross-sectional view of the catheter device of FIG. 1 shown with the needle assembly withdrawn and without the flexible tubing located in the fluid port;

FIG. 4A is an isometric view of an embodiment of a septum usable in a catheter hub of the present disclosure;

FIG. 5A is a cross-sectional view of an embodiment of a flexible tubing;

FIG. 5B is a cross-sectional view of another embodiment of a flexible tubing;

FIG. 7A is a top view of the catheter device of FIG. 1, shown with a flange of the needle assembly retracted in a proximal direction and about to contact the tube deflector to transition the tube deflector to an open position;

FIG. 7B is a top view of the catheter device of FIG. 7A, shown with the needle hub removed and the tube deflector of the catheter device in the open position;

DETAILED DESCRIPTION

Figure 4B:
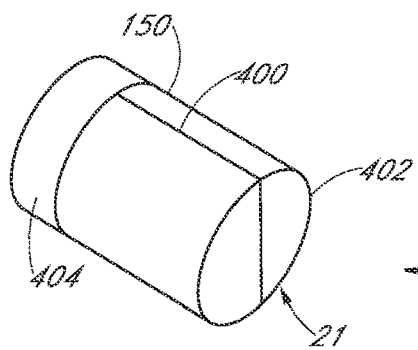
FIGS. 4B-4D show an alternative septum usable in a catheter hub of the present disclosure.

The detailed description set forth below in connection with the appended drawings is intended as a description of the presently preferred embodiments of catheter devices provided in accordance with aspects of the present assemblies, systems, and methods and is not intended to represent the only forms in which the present devices, systems, and methods may be constructed or utilized. The description sets forth the features and the steps for constructing and using the embodiments of the present assemblies, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

With reference now to FIGS. 1A and 1B, a catheter device or assembly 10, such as an over-the-needle catheter assembly or an IV catheter assembly, provided in accordance with aspects of the present disclosure is shown, which comprises a needle assembly 200, a catheter hub unit 90 comprising a catheter hub 120 having a catheter hub body 124 and a side port 125 extending from the catheter hub body 124, a catheter tube 140 extending distally from the catheter hub body 124, a connector 190 at an end of a flexible tubing 180, which is connected to the catheter hub 120, a septum 150 located in an interior cavity 123 (FIG. 3) of the catheter hub body 124, and a tubing management system 300 for managing the flexible tubing 180, as further discussed below. Also discussed below is another catheter assembly embodiment with a tubing management system 300 shown in FIG. 9A. The catheter device 10 of FIG. 9A comprises a needle assembly 200, a catheter hub unit 90 comprising a catheter hub 120 having a catheter hub body 124 and a side port 125 extending from the catheter hub body 124, a catheter tube 140 extending distally from the catheter hub body 124, a connector 190 connected to a flexible tubing 180, which is connected to the catheter hub 120, and a septum 150 (FIG. 9B) located in an interior cavity 123 of the catheter hub body 124, but having a different tubing management system 300 than the embodiment of FIGS. 1A and 1B for managing the flexible tubing 180. Because both embodiments of the catheter device of FIGS. 1A/1B and 9A/9B can use the same needle assembly 200, the needle assembly 200 will be discussed first, followed by the embodiments of the catheter device 10 shown in FIGS. 1A/1B and FIGS. 9A/9B. The needle assembly 200 may be structurally the same for both embodiments with some variations contemplated.

FIGS. 1A and 1B show the needle assembly 200 in a ready to use position comprising a needle hub 220, a needle 240 having a needle tip 245 projecting distally from a nose section of the needle hub 220 through a proximal end 121 of the catheter hub body 124 of the catheter hub 120, the septum 150, and in through the catheter hub 120 and the catheter tube 140 with the needle tip 245 extending out a distal end of the catheter tube 140 for accessing the vasculature of the patient. The needle hub 220 can have a cylindrical, rectangular, or any shape cross-section that can aid a user gripping the needle hub 220. Surface features, such as fins and bumps, may be added to further aid in the gripping. In the illustrated embodiment, the needle hub 220 has a rectangular cross-section with rounded edges. The needle hub 220 can further include a flashback chamber (not shown) and a proximal opening covered with a vent 270 to allow air or gas to escape as blood flows into the needle 240 and into the flashback chamber after a successful venipuncture. The vent 270 can be part of a vent plug or a blood stopper.

The needle 240 can be notched or non-notched, any acceptable gauge, and any acceptable length. In the case of a notched needle 240 having an opening near the needle tip 245, indication of successful venipuncture occurs when the needle tip 245 and the distal end of the catheter tube 140 enter the vasculature and blood enters the needle lumen and out the notched opening of the needle 240 and into the annular space between the catheter tube and the needle and into the catheter hub 120. In the case of a non-notched needle 240, blood enters through the lumen of the needle 240 and into the flashback chamber of the needle hub 220. Blood can also be drawn into a blood stopper connected to the proximal opening of the needle hub, similar to the blood stopper disclosed in U.S. patent application Ser. No. 14/576,802, filed Dec. 19, 2014. Once successful venipuncture has occurred, the needle assembly 200 can be detached and removed from the catheter hub 120.

Figures 9A, 9B:
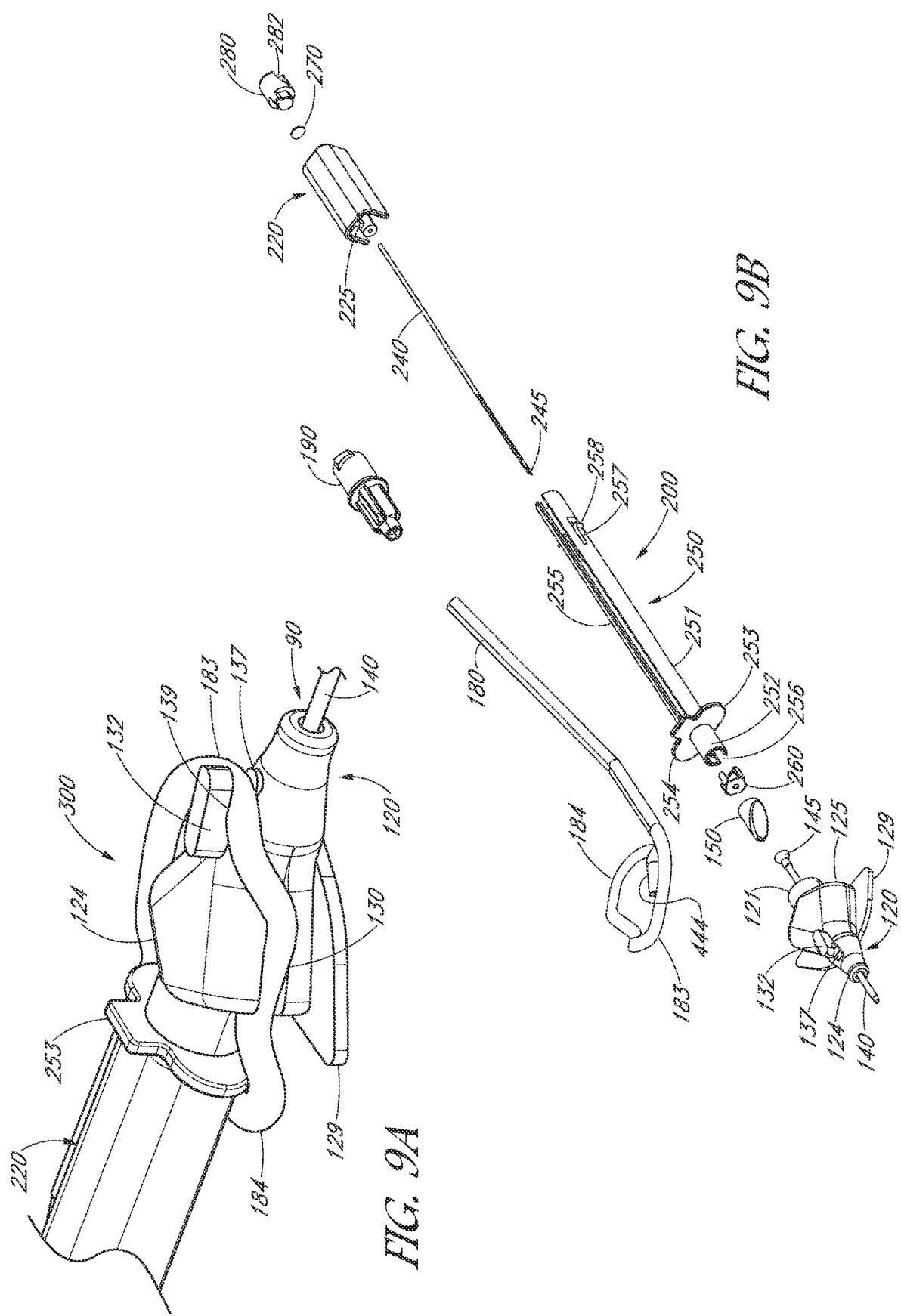
FIG. 9A is a partial isometric view of another embodiment of a catheter device of the present disclosure comprising an alternative tubing management system.
FIG. 9B is an exploded perspective view of the catheter device of FIG. 9A.

The needle assembly 200 can further comprise a needle shield 250 to shield, guard, cover, or secure the needle tip 245 of the needle 240 when the needle hub 220 is withdrawn proximally away from the catheter hub 120 from the ready to use position to a retracted position. As shown in FIGS. 1B and 9B, the needle shield 250 comprises a flange 253, a hollow proximal portion 251 extending proximally from the flange 253, and a hollow distal portion 252 extending distally from the flange 253. The distal portion 252 of the needle shield 250 is configured to extend into the interior cavity 123 (FIG. 3) of the catheter hub body 124 with the flange 253 abutting against a proximal end edge 121 of the catheter hub body 124 in the ready to use position. The proximal portion 251 of the needle shield 250 can be a hollow body having a slot 255 extending axially along the lengthwise axis of the hollow body. In one example, the slot 255 of the proximal portion 251 extends from the flange 253 to a proximal end edge of the proximal portion 251. The distal portion 252 can be a hollow body having a gap or a slot 256 extending axially along the hollow body. Thus, the present needle shield 250 is understood to include a proximal portion 251 and a distal portion 252 with each having a hollow cylindrical body and a lengthwise slot, wherein each portion has a C-shaped cross section due to the lengthwise slot. The two slots can be aligned or offset. The slot can vary in width and can be sized and shaped to allow a structure or feature to slide along the length of the respective slots.

The flange 253 has an area profile that is generally larger than the diameter or cross-sectional profile of the distal portion 252 and the proximal portion 251. The flange 253 can also have a larger profile than the proximal end 121 of the catheter hub body 124 so as to abut the proximal end 121 or at least limit further insertion of the distal portion 252 into the catheter hub in the catheter ready to use position. The flange 253 may or may not have flange extensions 254 extending radially outwardly relatively to the lengthwise axis of the device to engage and activate the tubing mechanism 300, as described below. In some examples, the flange 253 can have a shape of a two-leaf clover, a three-leaf clover, or a four-leaf clover. In other examples, the flange 253 can be round, oval, elliptical, or polygonal in shape. The length of the needle shield 250 can be selected so that in the needle retracted position following venipuncture, the needle tip 245 is recessed from the distal end edge of the distal portion 252.

After successful venipuncture, the needle hub 220 is slidable axially along the slot 255 of the proximal portion 251 from the ready to use position in which the needle hub 220 abuts against the flange 253 of the needle shield 250 or is in close proximity of the flange 253 to a retracted or secured position in which the needle hub 220 is substantially away from the flange 253. This movement of the needle hub 220 relative to the needle shield 250 has the effect of retracting the needle shaft and the needle tip into the needle shield 250. In an example, a tab 225 can be formed with the needle hub 220 to slide inside the slot 255 of the proximal portion 251 of the needle shield 250 to guide the needle hub 220 from the ready to use position to the retracted position. For example, the tab 225 can be incorporated to connect an elongated needle hub cylinder 80 of the needle hub to an outer shroud 82. In some examples, there can be two or more aligned tabs 225, which may also be referred to as fins. Thus, the slot 255 can confine the tab 225 to limit rotational travel of the needle hub 220 relative to the needle shield. The slot 255 can be closed off by a cap 280 fixed at a proximal end of the proximal portion 251 to prevent the tab 255 of the needle hub 220 from displacing proximally out of the slot 255, as illustrated in FIG. 1C. The cap can also incorporate other surface features to perform other functions, such as to temporarily secure the tubing 180 and/or the connector 190.

With reference to FIG. 1C, when the needle hub 220 is in the retracted position following use, the needle hub 220 can be prevented from moving from the retracted position with the needle tip shielded or covered by the needle shield 250 to re-expose the needle tip, such as to move the needle tip from the cover of the needle shield. In an example, the limiting mechanism to prevent re-exposure of the needle tip can be a catch 258 extending from a tab 257 located near the end of the proximal portion 251 of the needle shield 250. The tab 257 can be formed with three continuous slots on the shield body to create a cantilever spring portion. In an example, two or more combinations catch and tab can be incorporated on the needle shield. The catch 258 can engage the needle hub 220 in the retracted position to fixedly secure the needle hub 220 to the needle shield 250. In one example, as the needle hub 220 slides proximally away from the catheter hub 120 along the proximal portion 251 of the needle shield 250, the shroud 82 of the needle hub 220 gradually presses or deflects the catch 258 inwardly thereby elastically deflecting the tab 257 from its original state. Once the needle hub 220 is in the retracted position and the needle tip 245 is covered, the tab 257 and the catch 258 can elastically return back to its original state and engage a detent or shoulder on the needle hub 220 to restrict distal movement of the needle hub 220 relative to the needle shield 250. The catch 258 can have a tapered surface 306 at a distal portion to allow the needle hub 220 to gradually bias the catch 258 and the tab 257 inwardly towards the lengthwise axis. The catch 258 can also have a stepped surface 308 at a proximal portion of the catch 258 to prevent the needle hub 220 from biasing the catch 258 and the tab 257 inwardly once the needle hub 220 is in the retracted position, thus capturing the needle hub 220 in the retracted position.

In one example, the needle hub 220, for example the shroud 82, completely passes over the catch 258 and the catch 258 engages an internal shoulder, such as a detent or a recessed groove formed with the shroud 82 of the needle hub 220, to maintain the needle hub in the retracted position. In another example, the catch 258 can engage with a slot or opening (not shown) in the needle hub 220 to maintain the needle hub 220 in the retracted position. Other methods and mechanisms can also be used to prevent the needle hub 220 from moving distally relative to the needle shield 250 from the retracted position and is not limited to the mechanisms and structures described herein.

The needle assembly or device 10 can further comprise a spring clip 260 for removably securing the needle shield 250 to the catheter hub 120 in the ready to use position and during retraction of the needle hub 220 following successful venipuncture. The spring clip 260 can be located proximally of the septum 150 and secured to the distal portion 251 of the needle shield 250. The spring clip 260 can engage the catheter hub 120 when the needle 240 is in the ready to use position and can disengage from the catheter hub 120 when the needle 240 is in the retracted or secured position. FIG. 2 illustrates one embodiment of the spring clip 260 of the present disclosure, which comprises a wall 262 having an aperture 263 and a securing arm 265 extending proximally of the wall 262. As shown in FIG. 2, the spring clip is rotated from its normal use position, which typically has the arm 265 oriented towards the slot 256 of the distal portion 252 of the shield 250 so that the free end of the arm 265 can contact the interior cavity of the catheter hub through the slot 256, as further discussed below.

In an example, the spring clip 260 has a wall 262 having a proximally facing wall surface and a distally facing wall surface. The wall 262 can be generally circular or round and can include a circular or non-circular aperture 263 for the needle 240 to extend therethrough in the ready to use position. One or more supports 264 can extend in a proximal direction from the wall 262. The supports 264 are configured for attaching to the needle shield 250, such as to the distal portion 252 of the shield. The attachment between the supports 264 and the distal portion 252 can be by mechanical means, such as by interference or spring load, by welding, by snap fit, or by adhesive. For example, the one or more supports 264 can be sleeved to an inner surface or outer surface of the distal portion 252 of the needle shield 250 and form a tight interference fit to fix the spring clip 260 to the distal portion 252. The supports 264 of the spring clip 260 and therefore the spring clip 260 can be fixedly secured to the needle shield 250 in both the ready position and the needle retracted position or secured position. The spring clip 260 can further comprise a securing arm 265 having an elbow 266 extending from the wall 262, and a tip 267 at a free end of the arm 265. The elbow 266 can be L-shaped, can have an acute angle or an obtuse angle, and is configured to contact with and be biased outwardly by a side of the needle 240 in the ready to use position. The biasing by the needle on the elbow 266 causes the tip 267 at the free end of the arm 265 to project through the slot 256 of the distal portion 252 of the shield 250 to press against and removably engage with the interior cavity 123 of the catheter hub, such as to the proximal hub chamber 304 (FIG. 3) of the catheter hub body 124. This allows the spring clip 260 to secure the needle shield 250, to which the spring clip is fixedly secured, to the catheter hub body 124 until the biasing is removed, at which time the needle shield can separate from the catheter hub. In some examples, the tip 267 has a shaped lip for engaging a corresponding notch or detent in the interior of the catheter hub body.

In an example, the arm 265 has a length and each support 264 has a length. The supports 264 can also be considered or called arms extending from the wall 262. In one embodiment, the length of the arm 265 is longer than the length of each support 264. In another embodiment, the length of each support 264 is longer than the length of the arm 265. In still other examples, the arm can be longer than one support but shorter than a second or different support. Thus, the present disclosure is understood to be directed to a spring clip 260 comprising a wall 262 having a perimeter defining an opening 263, said wall having a distally facing wall surface and a proximally facing wall surface, and wherein a plurality of arms extend in a proximal direction. The plurality of arms can have different lengths. The spring clip 260 can be without any distally extending arms or arms that extend in the distal direction. In other examples, a partially enclosed structure having a shape of the interior of the distal portion 252 is incorporated with the spring clip 260 and the supports are omitted. The arm 265 can be located in the gap or space of the partially enclosed structure and the partially enclosed structure can be fixedly secured to the distal portion 252. In the embodiment shown, the spring clip 260 comprises a wall having an opening and two or more arms extending proximally from the proximally facing wall surface of the wall 262. In an example, the spring clip 260 can comprise three or more arms extending in the proximal direction from the wall 262 and wherein at least one of the arms is configured to contact and be biased by a side of the needle in the ready to use position to press against an interior of a catheter hub body. As described, the arm being biased can project through a gap of the needle shield to press against the interior of the catheter hub body.

In the ready to use position, the needle 240 projects through the septum 150 and through the spring clip 260 and biases the elbow 266 of the spring clip to bias the arm outwardly so that the tip 267 of the spring clip, which is at a free end of the arm, engages the catheter hub 120 to secure the needle shield 250 to the catheter hub 120. Thus, an aspect of the present disclosure is understood to include catheter device comprising a spring clip comprising a wall having a plurality of proximally extending arms and wherein the spring clip is secured to a needle shield and is biased by a needle into removable engagement with a catheter hub in a ready to use position. In example, at least one of the arms is fixedly secured to a distal portion of the needle shield. In an example, one of the arms is biased by the needle so that a free end of the biased arm projects through a slot on the needle shield to removably engage the catheter hub. In the ready to use position, the needle 240 presses against the elbow 266 to deflect it outwardly, which causes the tip 267 at the free end of the spring clip to engage or press against a surface or engagement mechanism in the interior cavity 123 of the catheter hub body 124. When the needle hub 220 and needle 240 are retracted proximally from the catheter hub 120 following successful venipuncture, the needle is moved proximally until the needle tip moves proximal of the elbow 266, which then frees the arm 265 from the bias of the needle 240. This allows the arm to move radially inwardly and the tip 267 at the free end of the arm 265 to space from the interior surface of the catheter hub. At this point, the elbow 266 elastically returns inwardly to its normal unbiased position or state, thereby disengaging the tip 267 of the arm 265 from the surface of the interior cavity 123 of the catheter hub body. With the tip 267 of the arm spaced from the interior surface of the catheter hub, the needle shield 250 no longer attaches to the catheter hub body 124 and the combination needle assembly 200 and needle shield 250 can now detach or separate from the catheter hub 120.

With reference now to FIG. 3, a cutaway view of the catheter hub 120 of FIG. 1 is shown, which comprises the catheter hub body 124, a side port 125 extending from the catheter hub body 124, and a pair of wings 129 extending from opposite sides of the catheter hub body 124 to provide additional surface area beyond just the area of the catheter hub to secure the catheter hub 120 to the patient. The wings 129 can be attached to the catheter hub body 124 by mechanical means, such as by snap fit, welding, or by fasteners, or be integrally molded to the catheter hub body 124. In the illustrated embodiment, the wings 129 are elastically deformable and integrally formed and extend radially outwardly from a bottom region of the catheter hub body 124. The wings 129 can have any number of shapes and can serve as a grip for the user to hold when using the catheter device 10. The side port 125 has a lumen 128 in fluid communication with the interior cavity 123 of the catheter hub body 124. The proximal end 121 of the catheter hub body 124 can have a female luer connector with a female luer taper and can include external threads to matingly receive a threaded male Luer. The external threads are also configured for engagement with the distal portion 252 of the needle shield 250. The side port 125 can be configured for delivering fluids, such as medicament, IV solution, or other fluids, to the patient rather than through the proximal end 121 of the catheter hub body 124, which can be sealed off by the septum 150 located inside the catheter hub 120.

The septum 150 is positioned in the interior cavity 123 of the catheter hub body 124 between the distal end 122 and the proximal end 121 of the catheter hub body 124 to isolate a distal hub chamber 302 from a proximal hub chamber 304 when the septum 150 is closed, such as after the needle is removed therefrom. The septum 150 can prevent fluid flow between the distal hub chamber 302 and the proximal hub chamber 304 and contain or limit fluid flow to the area between the distal hub chamber 302 and the lumen 128 of the side port 125. The septum 150 can be made of a biocompatible elastomeric material such as a silicone material. The septum 150 forms a seal with the interior wall surface of the interior cavity 123 of the catheter hub body 124. In one example, the septum 150 can be wedged or press fitted in the interior cavity 123 of the catheter hub body 124, thereby forming the seal between the septum 150, such as between the exterior wall surfaces of the septum, and the interior wall surfaces of the interior cavity 123. In another example, the septum 150 can be pushed against and engage between one or more circumferential projections (not shown) when assembling the septum 150 to the interior cavity 123 of the catheter hub body 124. The septum 150 can also be secured to the interior cavity 123 of the catheter hub by a securing mechanism (not shown), such as an additional holder or retaining ring ultrasonically welded to the catheter hub 120, or by using adhesive.

The design of the septum 150 can take on various shapes and forms as illustrated in FIGS. 4A-4M and further discussed below. Note however that the embodiments of the septum 150 discussed herein are merely examples and variations of the septum including septum designs not discussed herein can be used in the catheter device 10 of the present disclosure.

FIG. 4A illustrates one example of a septum 150 that can be cylindrical at a proximal end 151 and then slanted at a distal end 152, opposite the proximal end. The slanted surface 152 can match the angle of the side port 125, as shown in FIG. 3. The slant can taper into a small profile near a distal end edge of the septum. A slit or a slot 153 can extend from a wall on the proximal portion 151 to the distal portion 152 of the septum 150 and through the slanted surface. The slit 153 can expand or open to allow the needle 240 to project through the slit 153 of the septum in the ready to use position. Following use when the needle 240 is retracted proximally out the septum 150, the slit 153 seals or closes upon itself to prevent fluid from flowing therethrough.

The slit 153 can be formed from a line cut through the length of the septum.

In other examples, the septum 150 has a slanted distal wall as shown in FIGS. 3 and 4A and a hollow bore with a proximal wall having one or more flaps defined by one or more slits formed on the proximal wall. In an example, three slits intersecting at a point forming three flaps are utilized with higher or lower number of slits contemplated. The slits can form a seal around a shaft of the needle 240. After successful venipuncture, the needle 240 is retracted proximally out the septum 150. As the needle 240 slides out the septum, the flaps or portion of the septum 150 surrounding the opening where the needle just vacated can wipe the blood off the surface of the shaft of the needle 240. After the needle 240 is removed from the bore and the proximal wall with the flaps of the septum 150, a seal is formed at the slits to prevent blood from passing through the opening 153. That is, as the needle 240 is removed from the septum 150, the septum 150 forms a seal to prevent fluid passing through the septum 150 between the distal hub chamber 302 and the proximal hub chamber 304 after the needle 240 is withdrawn.

In another example, the septum 150 does not have any opening, bore or slit 153, just a solid core. But because the septum 150 can be made from an elastic material, such as silicone, rubber or other elastomeric material, it acts as a plug that can be pierced by the needle 240. The plug can seal upon itself upon retraction of the needle thereby preventing fluid from passing through the septum 150.

In another example, the septum 150 can have a cavity (not shown) that can trap fluid or house a fluid absorbent material therein. The cavity can extend to one end of the septum 150, such as distal of the proximal wall, or be confined between opposite ends of the septum 150. The cavity can be cylindrical or any other shape.

The distal end 152 of the septum 150 of FIG. 4A can be shaped to smoothly direct fluid flow between the distal hub chamber 302 and the lumen 128 of the side port 125 after the needle 240 is removed from the septum. For example, the distal end 152 of the septum 150 can be chamfered or curved so that the directed fluid can flow in either direction between the catheter tube 140 and the flexible tubing 180 attached to the side port 125.

Figure 4D:
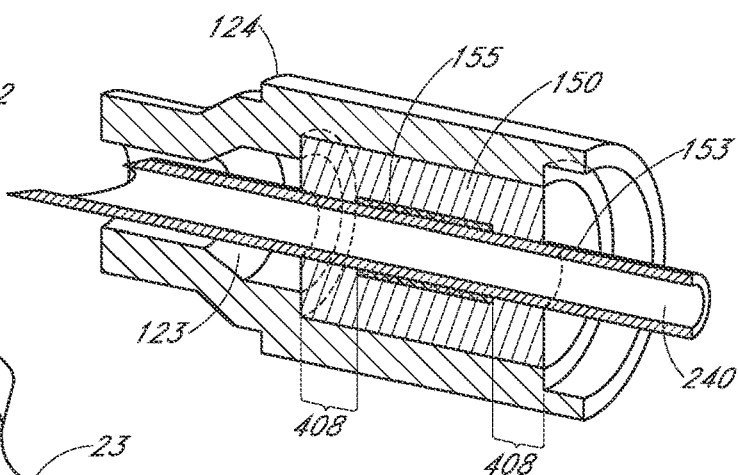
Figure 4C:
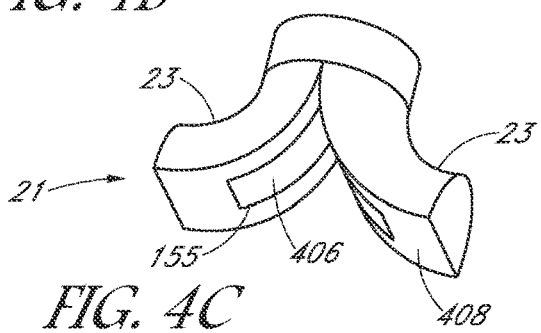

FIGS. 4B-4D illustrate another example of a septum 150 provided in accordance with aspects of the present disclosure. The present septum 150 may be referred to as a split septum having a split 400 extending partially along a length of the septum 150. Referring to FIGS. 4B and 4C, the septum 150 can be split entirely into two or more equal or unequal portions from a first end 402 of the septum 150 to a second end 404 of the septum 150, which is a base portion without a split forming through the outer circumference. The first end 402 with the split 400 forms a first end portion 21 having a plurality of legs 23 extending from the base portion 404. The legs 23 can have equal or different sizes, such as different thicknesses formed by providing the split 400 off-center. At the end wall of the base portion 404, a slit 153 is provided similar to the slit of FIG. 4A. The slit 153 at the base portion 404 communicates with the split 400 on the first end 402.

Interiorly of the septum 150, a recess 406 is formed into each of the two legs 23 so that when the two legs contact one another, the two recessed sections 406 form a cavity 155 within the septum 150. The cavity 155 can be generally cylindrical in shape and bounded at two ends by a septum wall section 408 having a slit, or a slit that is part of a split. In other examples, the cavity 155 can be other than cylindrical in shape. As shown, the slit at the first end 402 is formed completely across a diameter of the septum wall section 408. The slit 153 at the second end or base portion 404 is not formed completely across a diameter of the septum wall section 408 of the base portion. In use, as further discussed with reference to FIG. 4D, the cavity 155 of the septum 150 is configured to trap fluid or house a fluid absorbent material to absorb fluid, such as blood, that may flow around an exterior of the needle shaft, such as during secondary flashback.

When the split septum 150 is placed inside a catheter hub body 124 as shown in FIG. 4D, which can be similar to the hub body of FIG. 3 having a side port, the split septum 150 forms a seal with the interior surfaces of the interior cavity 123 of the catheter hub body 124, which imparts a radial compressive force on the split septum to close the slit 152 at the base portion 404 and the split 400 at the first end 402. A needle 240 is shown projecting through the septum wall section 408 with the slit 153 at the second end 404, the cavity 155, and the septum wall section 408 of the first end 402 with the split 400. During retraction of the needle 240 following successful venipuncture, any blood on the outside of the needle can be wiped by the two septum wall sections 408 of the septum and be trapped or confined to the cavity 155.

Figure 4E:
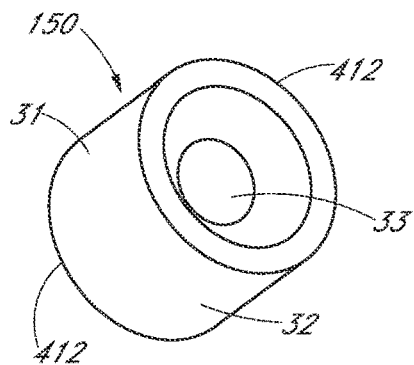
FIG. 4E-4F show another alternative septum usable in a catheter hub of the present disclosure.
Figure 4F:
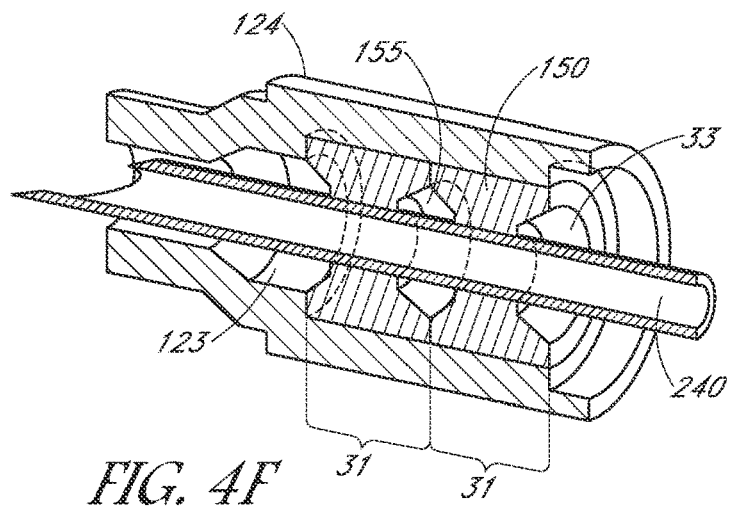

FIGS. 4E and 4F show another example of a septum 150 provided in accordance with aspects of the present disclosure. In the present example, the septum 150 can comprise two septum sections or septum pieces 31 arranged serially in the interior cavity 123 of a catheter hub body 124, as shown in FIG. 4F, which can be similar to the catheter body of FIG. 3 having a side port. The two septum pieces 31 can be identical or different from one another and can contact or be spaced apart from one another. In one example, each septum piece 31 comprises a body 32 having a cylindrical contour and two ends 412 and wherein each end has a concave portion 33. In an example, the concave portion 33 is formed by a frustoconical shape void, a spherical shape void, or other surface sections forming a concave surface. The concave portion 33 at each of the two ends 412 of the septum piece 31 can have a same or different depth and shape. In an alternative embodiment, the septum piece 31 can have one concave portion 33 on one end 412 and no concave portion at the other end 412. When two septum pieces 31 are arranged serially in the interior cavity 123 of the catheter hub body 124 as shown in FIG. 4F, a cavity 155 is formed by two adjacent concave portions 33 of two adjacent septum pieces 31. A seal is formed between the exterior of each of the two septum pieces 31 and the interior surface of the interior cavity 123 of the catheter body 124, such as by sizing the exterior dimensions of the septum pieces to be slightly larger than the interior dimension of the catheter body to create a compressive fit between the two. A slit 153 can extend through the body 32 of the two septum pieces 31 to facilitate insertion of the needle 240 through the septum 150. Upon removal of the needle 240, the inward compression on the septum pieces by the catheter hub will cause the slits 153 to automatically close. Fluid on the outside of the needle 240, such as blood from secondary flashback, can be wiped by one or both slits 153 and retained within the cavity 155 during retraction of the needle following successful venipuncture.

Figure 4G:
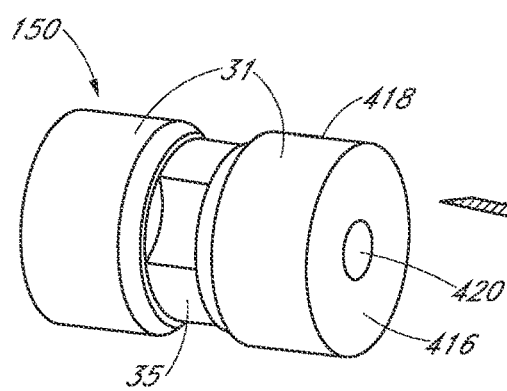
FIG. 4G-4H show yet another alternative septum usable in a catheter hub of the present disclosure.
Figure 4H:
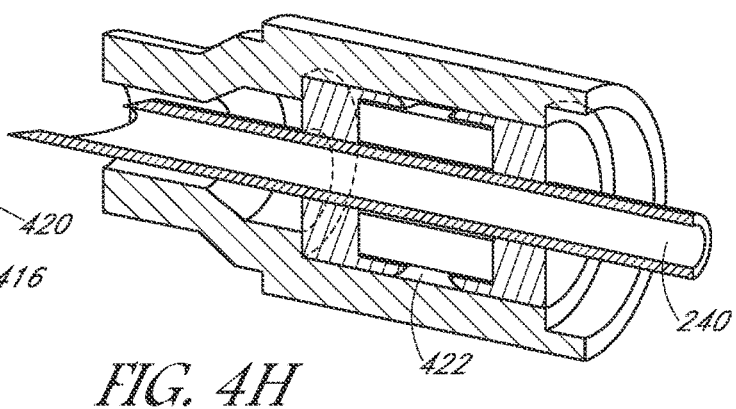

FIGS. 4G and 4H show another septum 150 in accordance with alternative aspects of the present disclosure. In the present embodiment, the septum 150 includes two septum pieces 31 and a sleeve 35 sandwiched between the two septum pieces 31. Each septum piece 31 of the present embodiment resembles a cap, which is understood to include a wall 416 and a cylindrical skirt 418 extending from the wall 416. The wall 416 can further include a perimeter 420 defining an opening that is sized and shaped to accommodate a needle shaft, in a size-on-size fit, loose fit, or interference fit. The interior of the cylindrical skirt 418 of the septum pieces 31 can be sized and shaped to accept the sleeve 35 when the septum pieces 31 are arranged serially inside the interior cavity 123 of the catheter hub body 124. In an example, when so arranged in the interior cavity 123, the two skirts 418 contact one another at the axial end of each. In the present embodiment, the two skirts 418 do not contact one another and a gap 422 is provided between the two, which exposes the sleeve 35 at an area between the two cylindrical skirts 418. The sleeve 35 can be cylindrical in configuration and can include a bore or lumen and be made from a similar material or different material than the septum pieces 31. For example, the sleeve 35 can be made from a material that has hydrophilic properties or liquid absorbing properties. The bore of the sleeve 35 may also be provided with a coagulating agent. Following successful venipuncture, the needle 240 can be retracted from the septum 150. During the retraction step, blood on the exterior of the needle 240 can be wiped by one or both openings on the two walls 416 and be captured or retained inside the bore of the sleeve 33.

Figure 4I:
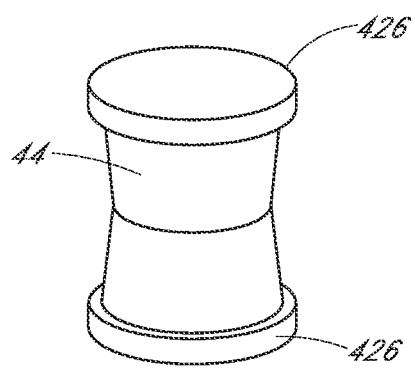
FIGS. 4I-4M show yet another show an alternative septum usable in a catheter hub of the present disclosure.
Figure 4J:
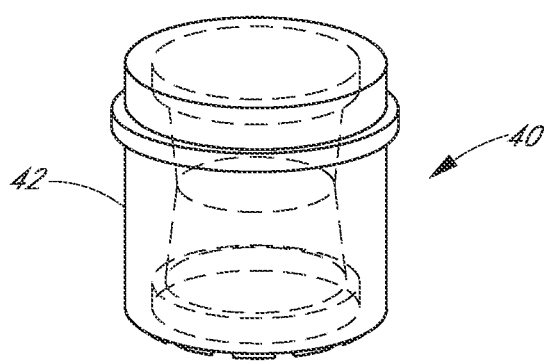
Figure 4K:
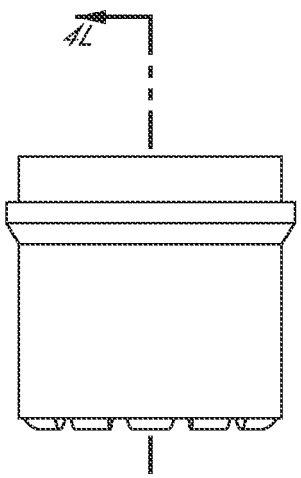
Figure 4L:
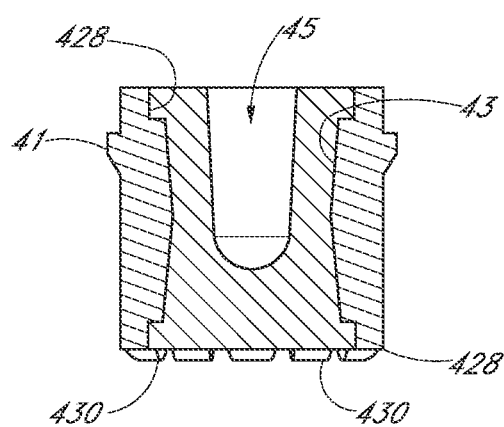
Figure 4M:
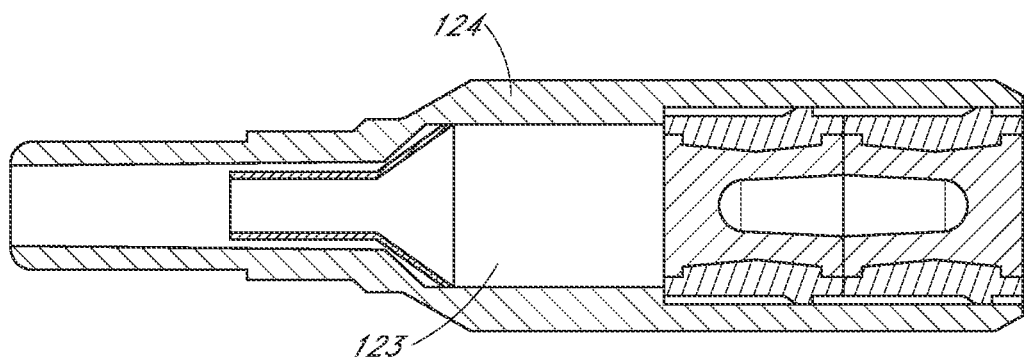

FIG. 4M illustrates yet another example of a septum 150 provided in accordance to further aspects of the present disclosure, which is shown positioned inside the interior cavity 123 of a catheter hub body 124 and shown without a needle projecting through the septum 150. The septum 150 may embody a multi-piece septum structure. With reference initially to FIG. 4J, in the present embodiment, the septum 150 can include two identical septum bodies 40. Each septum body 40 can have a septum housing element 42 and a septum sealing element 44 (FIG. 4I) received in an interior cavity of the septum housing element 42, as shown in dash-lines in FIG. 4J. Together, the combination septum housing element 42 and septum sealing element 44 can form a septum body 40.

With reference to FIGS. 4K and 4L in addition to FIGS. 4I and 4J, each septum housing element 42 can include a tapered internal surface for receiving a correspondingly shaped septum sealing element 44. In an example, the internal surface embodies an hourglass-shaped chamber 43. The taper in the chamber 43 forms a tight fit with the septum sealing element 44, similar to a size-on-size fit, which helps to reduce relative movement, such as translational movement, between the septum sealing element 44 and the septum housing element 42. The septum sealing element 44 can further include first and second flanges or shoulders 426 and the septum housing element 42 can include first and second undercuts 428 formed in the chamber 43 for accepting the flanges or shoulders 426, as shown in FIGS. 4L and 4M.

Each septum housing element 42 can further include an external annular flange 41 or other protrusion to press into the internal cavity of the catheter hub body 124, which is shown without a catheter tube for clarity and can be similar to the catheter body 124 of FIG. 3. The arrangement between the septum housing element 42 and the catheter hub body 124 can help to reduce translational movement between the two.

The two septum bodies 40 can be arranged back to back so that they contact one another at an end inside the catheter hub body 124. In some examples, the two may be coupled together either before or after insertion into the catheter hub body 124 through interference fit, ultrasonic welding, epoxy or adhesive, threads, and/or any suitable coupling mechanism. As shown, the septum housing element 42 incorporates weld beads so that the two septum housing elements 42 can be welded together end-to-end prior to insertion into the catheter hub. Each septum sealing element 44 can include a cavity 45 that extends inward from an open end opposite a closed end such that when the two septum bodies 40 are assembled in the catheter hub body 124, the two open ends of the septum sealing element 44 from each septum body 40 can face or aligned to abut against each other. In this manner, as shown in FIG. 4M, the two cavities 45 can form an enclosed septum cavity 155 between two closed ends of the septum sealing elements 44. A path 153, such as a slit or an opening, can extend through the septum sealing element 44 of each septum body 40. As discussed above for the septum in FIG. 4A, a distal end of the various septums 150 discussed in FIGS. 4B-4M can be chamfered or curved so that the directed fluid flow in either direction between the catheter tube 140 and the flexible tubing 180 can be made relatively smoother.

Referring back to FIGS. 1A, 1B and 3, the catheter tube 140 extends distally from the distal end 122 of the catheter hub body 124. A proximal end of the catheter tube 140 can be attached to the distal end 122 of the catheter hub 120 by a bushing 145, which is conventional. The needle 240 projects through the catheter tube 140 and the needle tip 245 extends out a distal end of the catheter tube 140 in the ready to use position. The distal end of the catheter tube 140 can taper inwardly or have a smaller inner diameter than the rest of the catheter tube 140, and smaller than the outside diameter of the needle shaft, to form a seal between the distal end and the shaft of the needle 240. After successful venipuncture and as the needle 240 is retracted proximally from the catheter tube 140, blood can flow through the catheter tube 140 around the outside of the needle and into the distal hub chamber 302, which is in fluid communication with the flexible tubing 180 through the lumen 128 of the side port 125.

The flexible tubing 180 has one of its ends connected to the side port 125, as shown in FIG. 1A. The other end of the flexible tubing 180 can couple to a connector 190 to deliver or withdraw fluid between the patient and the connector 190. Typically the longer the flexible tubing 180, the greater is the freedom in positioning and orienting the connector 190 and preventing accidental pullouts. The flexible tubing 180 can be a traditional tubing section or can be a kink-resistant tubing to avoid restricting fluid flow through the flexible tubing and give the user or practitioner more freedom to route the flexible tubing in various ways, such as to bend or to manipulate the tubing, to accommodate placement of the connector 190 at any number of locations on or about the patient during use. In an example, the flexible tubing 180 can be made kink-resistant by having a non-circular tubing bore 186. FIG. 5A shows one example of a kink-resistant tubing 180 in cross-section with a circular outer circumference and a non-circular tubing bore 186. As shown, the non-circular tubing bore 186 has a triangular shaped cross-section. The apex of the three corners of the triangular bore can be pointed or radiused as shown. In other examples, the non-circular tubing bore can have a polygon shape, such as a pentagon or a heptagon. The non-circular tubing bore 186 allows the flexible tubing 180 to curve sharply without kinking. The flexible tubing 180 can also be made kink-resistant by having a non-circular outer circumference 188, with or without a non-circular tubing bore 186. FIG. 5B shows an example of a kink-resistant tubing 180 in cross-section having a non-circular outer circumference 188, which is cam shaped or teardrop shaped with a non-circular triangular tubing bore 186 that can instead be practiced with a traditional circular bore. In this example, the tubing material volume at tubing location A has a smaller radii of curvature along an outer contour and has a greater material volume than the tubing section at tubing location B, which has a larger radii or curvature along an outer contour. Viewed differently, the greater material volume at tubing location A can be added onto a normal round tubing outer contour. An external force can be applied to the kink-resistant tubing and bending the flexible tubing 180 to form a J-loop bend or bending the kink-resistant tubing in various other ways to position the connector 190 for use with minimal risk of completely blocking fluid flow due to tubing kinking. After the external force applied to the flexible tubing 180 is removed, the flexible tubing 180 can recover to its original shape or at least restore much of its original shape.

Referring again to FIGS. 1A and 1B, the connector 190 has a distal end 192 coupled to the flexible tubing 180 and a proximal end 191 configured to receive an IV connector or other fluid connection devices, such as a syringe tip or an IV adaptor, for fluid delivery, such as for delivery of medicament, IV solution, or other fluids, through the catheter hub body. In one example, the proximal end 191 of the connector 190 can be a female Luer connector with optional external threads to form a threaded female Luer. The female Luer connector is configured to matingly receive a male Luer connector, such as an IV line, a Luer access connector, a syringe tip, a vent plug, other known connectors or future-developed IV devices. Each of these components can be sized and shaped in conformity with at least some of the International Standards Organization (ISO) standards for female and male Luer connections under current or future standards. For discussion purposes, any one of these components or the class of these components may be referred to as a male medical implement for use with a female Luer. The location and orientation of the connector 190 for line connection with respect to the catheter insertion point depends on the length of the flexible tubing 180 and the tubing management system 300.

The tubing management system 300 of the present disclosure is configured to route the flexible tubing 180 to a predetermined or desired position for line connection, maximize the length of flexible tubing available for line connection, minimize tube kinks, and/or provide a J-loop bend to prevent accidental pull outs, as will be discussed below. Different embodiments of the tubing management system 300 are illustrated in FIGS. 1A, 1B, 6A, 6B, 7A, 7B, 9A, and 9B, among others. A first exemplary tubing management system 300 is shown with the catheter hub 120 in FIGS. 1A and 1n exploded view in 1B. The same tubing management system 300 is shown in detail in FIGS. 6A, and 6B, away from the catheter hub 120. The tubing management system 300 can be coupled to the catheter hub 120, such as formed with or attached to the catheter hub body 124, and comprises a clamp 168. In other examples, the tubing management system 300 can be molded as a unitary structure or be fixedly attached to the catheter hub 120. The flexible tubing 180 is received in the clamp 168 and held to the catheter hub body 124 by the clamp 168. In one example, the clamp 168 can be a C-shaped clamp having an opening 167 with a width sized and shaped to receive the flexible tube 140 and a cavity 169 for holding the flexible tube 180. The cavity 169 can be smaller than a smallest width of the flexible tube 180 so that the flexible tube 180 can be squeezed when pushed through the opening 167 and into the cavity 169 of the clamp 168 and be retained in the cavity 169. The width of the opening 167 of the clamp 168 may be the same or smaller than the smallest width of the flexible tubing 180 to prevent the flexible tubing 180 from slipping out of the cavity 169 after the flexible tubing 180 has been secured in the clamp 168. For example, if the flexible tubing 180 has a noncircular outer circumference 188, the smallest width of the flexible tubing 180 can be larger than the width of the opening 167 to prevent the flexible tubing 180 from displacing from the cavity 169 through the opening 167. In some examples, the opening 127 of the clamp may have a lip for limiting the flexible tubing from slipping out of the opening but the relative sliding movement between the flexible tubing and the interior wall surface of the clamp 168 is possible.

With reference to FIG. 1C, a notch 282 on the shield 250 of the needle assembly 200 can be utilized to removably hold a portion of the flexible tubing 180 remote from the clamp 168, such as near the connector 190 in the ready to use position. The notch 282 can be located on a cap 280 attached to the proximal end of the needle shield 250. The cap 280 can have a cylindrical shaped body 430 with the notch 282 formed therein and a rectangular projection 432 extending out a distal end to frictionally engage the shield 250 at the slot 255. Optionally, detents, adhesive, or other attachments means may be incorporated for attaching the cap to the shield 250. In other examples, the notch 282 or other holding structures, such as a clamp, can be incorporated directly with the shield, such as being co-molded, over-molded, or unitarily formed with the shield. A tubing section adjacent the connector 190, the connector 190, or both can be supported by the notch 282 to support the weight of the connector 190 as the catheter device 10 is inserted into the patient to access the patient's vasculature. The notch 282 also effectively supports the connector 190 when the catheter device 10 is packaged neatly inside a blister pack or other packaging material. The notch 282 also keeps the connector 190 and the flexible tubing 180 from hindering or obstructing the user during use on a patient.

Figure 6B:
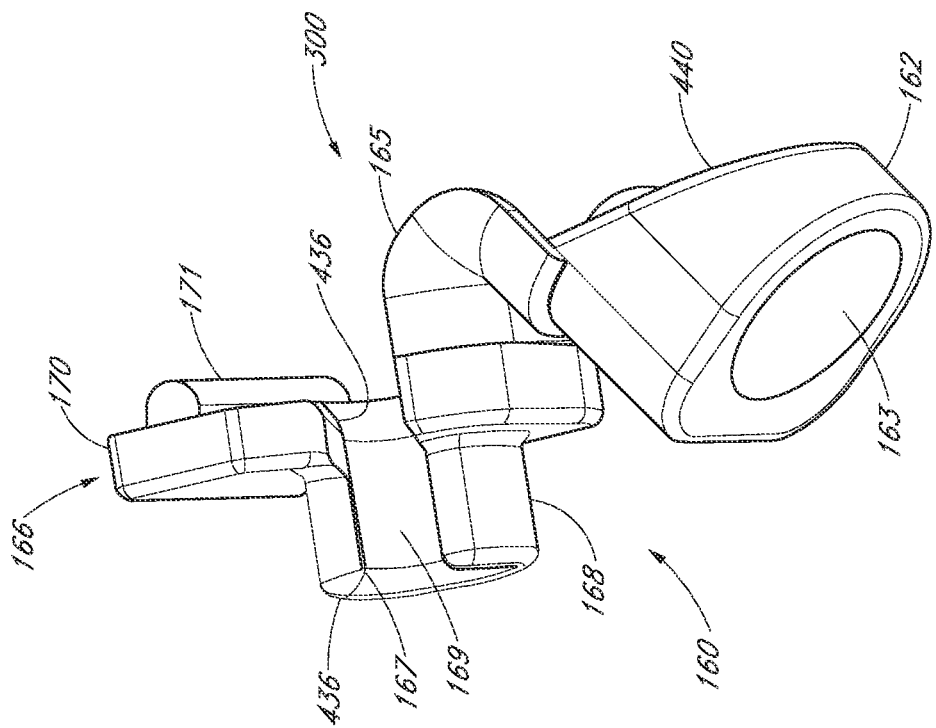
FIG. 6B is an isometric view of the tube deflector of FIG. 6A shown in an open position.
Figure 6A:
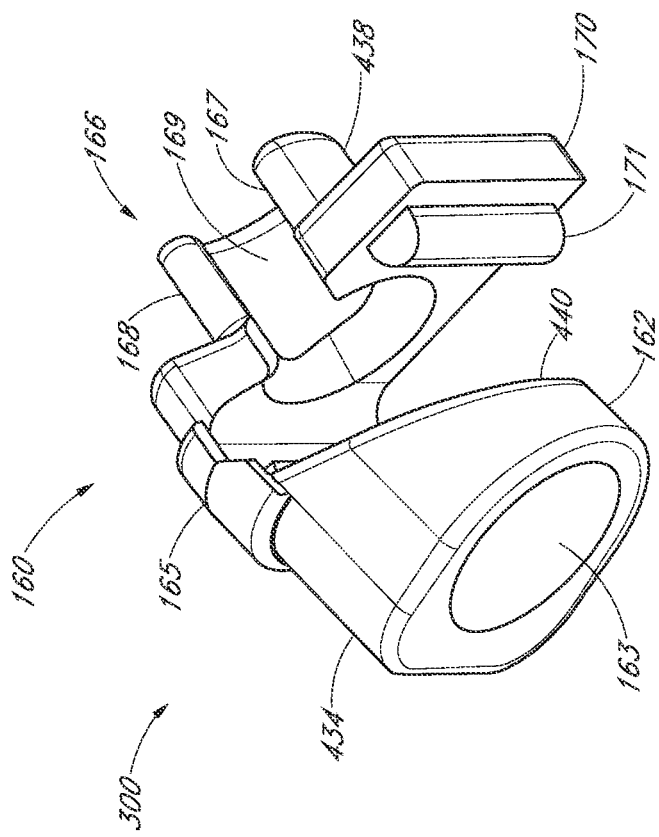
FIG. 6A is an isometric view of an embodiment of a tube management system having a tube deflector in a ready to use position.

With reference again to FIGS. 1A, 1B, 6A and 6B, the tubing management system 300 further comprises a tube deflector 160 comprising a base 434 and a deflector arm 166 coupled to the base 434 by a hinge 165. The clamp 168 may be located on or be part of the tube deflector 160. In some examples, the tube deflector 160 is integrated with the catheter hub and the base is omitted. In the present embodiment, the base 434 comprises a collar 162 for coupling to a side port 125 of the catheter hub body, such as for positioning over the side port 125 and receiving the side port 125 inside the hole 163, as further discussed below. The deflector arm 166 of the tube deflector is rotatable about the hinge 165 from a ready to use position shown in FIG. 6A to an open position shown in FIG. 6B, which shows the deflector arm 166 swinging away from the base 434. With reference to FIGS. 1A, 6A, and 7A, in the ready to use position, the flexible tubing 180 is secured to the side port 125 and extends through and held by the clamp 168. The flexible tubing 180 extends in the proximal direction from the side port 125 and is connected to the connector 190, as previously discussed. In this position, the length of the flexible tubing 180 should be long enough to extend from the side port 125 to the notch 282.

After successful venipuncture, the deflector arm 166 of the tube deflector 160 can be pivoted with respect to the base 434 about the hinge 165, such as by gripping the connector 190 and moving the connector so that the flexible tubing 180 causes the deflector arm 166 to rotate. A user can also grab the deflector arm 166 directly to rotate the deflector arm 166 about the hinge 165. In some examples, the deflector arm 166 is automatically rotated by the proximal movement of the needle assembly, as further discussed below. Movement of the deflector arm 166 causes the flexible tubing 180 to form a bend as the deflector arm 166 pivots from the ready to use position shown in FIG. 6A to the open position shown in FIG. 6B. In this position, a J-loop or U-shaped bend 184 is formed, as shown in FIG. 7B. During the rotation of the deflector arm 166, the flexible tubing 180 slides inside the internal cavity 169 of the clamp 168 while the clamp 168 biases and bends the flexible tubing 180 to form the U-shaped bend or J-loop 184, as it is more commonly known in the industry.

The clamp 168 can surround, loosely hold, or grip the flexible tubing 180. The clamp 168 and the flexible tubing 180 can slide freely relative to one another or there can be some resistance as the deflector arm 166 of the tube deflector 160 rotates from the ready to use position to the open position and moves relative to the flexible tubing 180. In one example, the interior cavity 169 of the clamp can be slightly larger than the flexible tubing 180 so that the flexible tubing 180 can slide freely relative to the clamp. In another example, the interior cavity 169 of the clamp can be substantially equal to the flexible tubing 180 to provide some resistance to the flexible tubing 180 when sliding inside the interior cavity 169 of the clamp. In yet another example, the interior cavity 169 can be slightly smaller than the outside diameter of the flexible tubing to produce a clamping force against the flexible tubing 180. For example, the clamp 168 can have an inner diameter greater than an outer diameter or size of the flexible tubing 180. In another example, the clamp 168 can have an inner diameter smaller than or equal to an outer diameter or size of the flexible tubing 180, such that the clamp 168 provides an elastic clamping force on the flexible tubing. However, for this example, the clamp 168 should be flexible enough to expand such that the flexible tubing 180 is slidable within the clamp 168.

The length of the clamp 168 measured between two open ends 436 can also affect the resistance of the deflector arm 166 to pivot because the relatively longer length can lead to a larger frictional surface area and/or can prevent the flexible tubing 180 from bending inside the clamp 168. A relatively shorter length of the clamp 168 measured between the two open ends 436 may produce less resistance than a relatively longer clamp 168.

The opening 167 of the clamp 168 can be selected to control the relative ease or complexity of installation of the tube inside the clamp. For example, a relatively large opening allows the flexible tubing 180 to slide freely inside the interior cavity 169 of the clamp during assembly prior to use of the catheter device 10 while a relatively smaller opening will require deflecting or compressing the flexible tubing, at least partially, to enable insertion into the interior cavity 169. The opening 167 also permits the clamp 168 to expand elastically to accommodate the flexible tubing 180 as the clamp 168 pivots about the side port 125. For example, the clamp 168 can be relatively thin and/or made from a flexible material so that when deflected, the clamp will give to enable flexing. When the deflector arm 166 of the tube deflector 160 rotates towards the open position of FIGS. 6B and 7B, the flexible tubing 180 can slide along the clamp 168 and form the rounded bend, such as the U-shaped bend or J-loop bend 184.

The deflector arm 166 of the tube deflector 160 can further comprise a flange 170. The C-shape body 438 of the clamp 168 can extend from the flange 170 along one or both sides of the flange 170. As shown, the C-shape body 438 extends in the proximal direction only out the proximally facing surface of the flange 170 when the flange is in the ready to use position of FIG. 6A. Generally, the clamp 168 can be aligned such that the axis of the clamp 168 is orthogonal to the axis of pivot to minimize resistance to rotation about the pivot or hinge 165.

A bumper 171 can extend from the flange 170 of the deflector arm 166 of the tube deflector 160 in a direction towards the base 434 in the closed or ready to use position of FIGS. 6A and 7A. The bumper can be sized to increase or decrease the gap between the surface of the flange and the flange extension on the needle shield, as further discussed below. The flange 170 and the bumper 171 can present a gripping area for a user to grasp the deflector arm 166 and pivot the deflector arm 166 from the ready to use position of FIG. 6A to the open position of FIG. 6B. Alternatively, a structure on the needle assembly can abut and push against the flange 170, the bumper 171, or both to passively move the deflector arm 166 to the open position.

With reference to FIG. 7A, the shield extension 254 of the shield flange 253 on the shield 250 overlaps with the flange 170 and/or the bumper 171 in a radial direction relative to the lengthwise axis of the catheter assembly or device 10. In other words, the flange 170, the bumper 171, or both stand along the pathway of the shield extension 254 of the needle shield. Consequently, when the needle assembly 200 is retracted from the catheter hub following successful venipuncture, the shield extension 254 pushes against the bumper 171 in the proximal direction, which causes the deflector arm 166 to pivot from the ready to use position of FIG. 7A to just past a threshold point of the hinge 165, which can be a living hinge. This threshold point is defined by a point in which the stress/strain of the hinge 165 causes the hinge to change its position and continue its rotation to the open position shown in FIGS. 6B and 7B. The threshold pivot point can prevent the deflector arm 166 from prematurely or unintentionally pivoting to the open position until a sufficient force physically initiates the pivot of the deflector arm 166 past a certain distance.

In an example, as the needle 240 and the needle hub 220 are retracted proximally away from the catheter hub 220 following use, the shield flange 253 will move proximally away from the catheter hub 120 after the spring clip 260 disengages from the catheter hub 120, as previously described. As the shield flange 253 moves proximally, the shield extension 254 presses against the flange 170 and/or the bumper 171 and the deflector arm 166 will begin to pivot. As the needle assembly 200 continues to be withdrawn in the proximal direction, the shield extension 254 continues to push against the deflector arm 266 of the tube deflector 260 while the clamp 268 and the flexible tubing 180 slide relative to one another and forces the flexible tubing to bend to form a J-shaped loop 184. Once the pivot point threshold is reached, the tube deflector 160 swings automatically completely to the open position. That is, the deflector arm 166 can swing to the open position without additional external force and the deflector arm 166 can therefore open passively without additional external force. In an example, the hinge 165 of deflector arm 166, once the pivot threshold is reached, can overcome the resistance between the clamp 168 and the flexible tubing 180, as well as the force required to bend the flexible tubing 180, to swing the deflector arm 166 to the open position. Thus, the present needle assembly 10 is understood to include a passive tubing management system 300 that automatically orientates the tubing and forms a J-loop in the flexible tubing upon retraction of the needle hub from the catheter hub following successful venipuncture. As described, the present disclosure utilizes a structure on the needle assembly 200 to initiate a pivot of the deflector arm 166 during normal retraction of the needle assembly following successful venipuncture. Once the deflector arm 166 pivots a certain amount beyond the pivot threshold of a hinge 165, the stress/strain on the hinge automatically pivots the remaining rotational movement to cause a J-loop to form in the flexible tubing and the flexible tubing to change its orientation, as previously discussed.

The needle assembly 200 can be completely detached from the catheter hub 120 as previously discussed with the tube deflector 160 rotated to the open position shown in FIG. 7B until forcibly returned to the closed or ready to use position, such as by hand. By orienting the end of the flexible tubing 180 with the connector 190 in the same orientation as the insertion direction of the catheter tube 140, the J-loop bend 184 of the flexible tubing 180 can reduce the probability of accidental pullout of the flexible tubing 180 from the catheter hub 120 or the catheter tube 140 from the patient.

Figure 8:
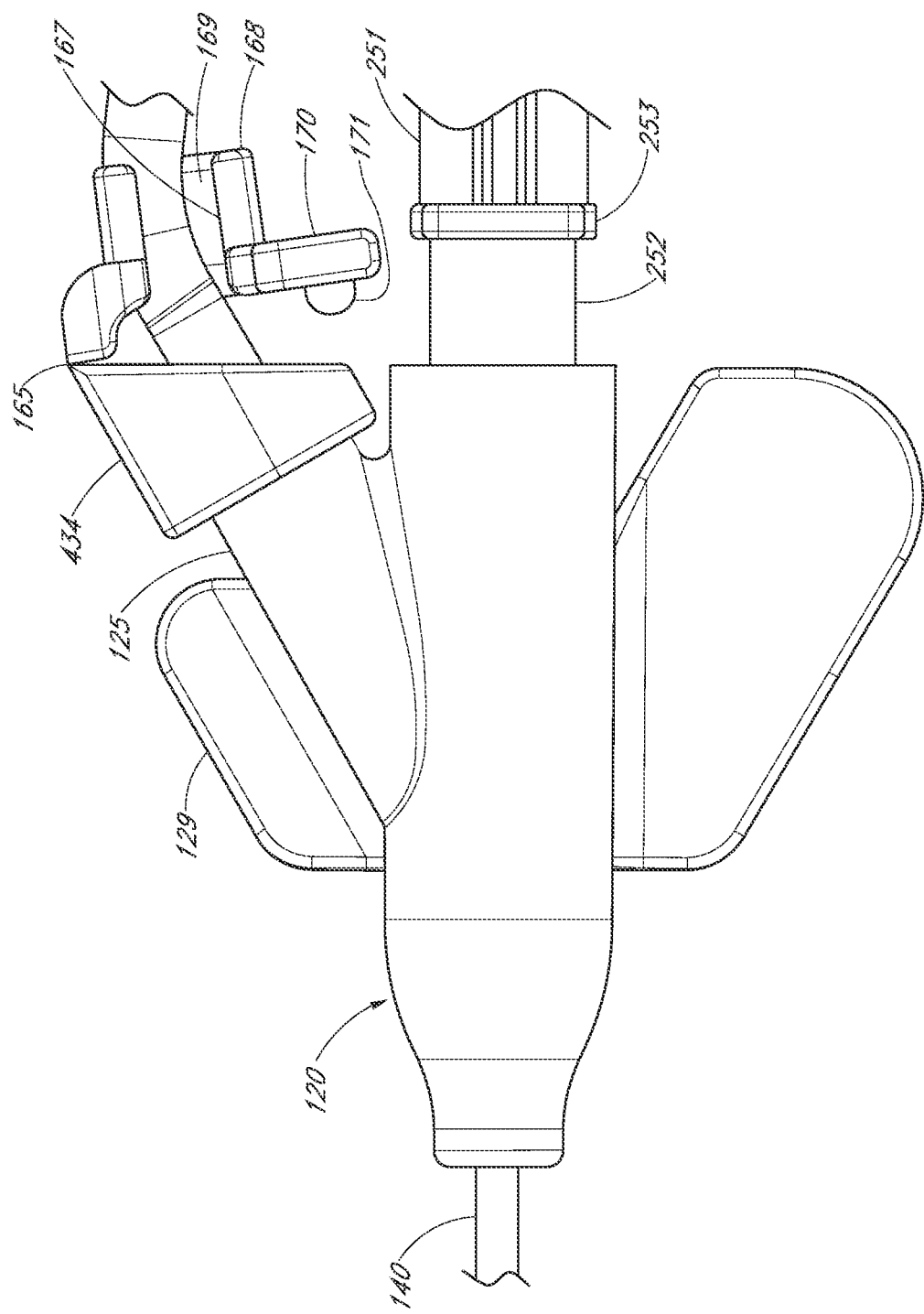
FIG. 8 is a partial top view of another embodiment of a catheter device having a needle assembly without a shield flange and a tubing management system.

Referring now to FIG. 8, an alternative catheter device 10 is shown that is similar to the catheter device of FIGS. 7A and 7B. However, in the present embodiment, the needle shield 250 does not have a shield flange 253 or a shield extension 254, as shown in FIG. 7A. Thus, upon retraction of the needle assembly 120, the deflector arm 166 on the tubing management system 300 will not automatically rotate by the needle assembly 200 to form a J-loop in the flexible tubing 180. Instead, a separate external force apart from simply retracting the needle assembly in the proximal direction is needed to pivot the deflector arm 166. In an example, the external force is digital pressure or force applied to the deflector arm 166 to rotate the arm about the hinge. Alternatively, a user can grip the connector 190, the tube 180, or both to rotate the deflector arm 166. The tubing management system 300 of the present embodiment is thus an active system requiring a separate force other than the retraction force of the needle assembly 200 to remove the needle hub and the needle in the proximal direction to manually swing the deflector arm 166 of the tube deflector 160 from the closed or ready to use position to the open position prior to, during, or after the needle hub 220 and the needle 240 are withdrawn from the catheter hub 120.

Similar to the aforementioned passive tubing management system of FIGS. 7A and 7B, as the deflector arm 266 of the tube deflector 260 is pulled or pushed by a user against the flange 170 or bumper 171, the flexible tubing 180 slides relative to the clamp 268 of the deflector arm 166 and begins to bend. Once the pivot point threshold of the hinge 165 is reached, the deflector arm 166 of the tube deflector 160 swings to the open position. The needle 240 and needle hub 220 can be completely detached from the catheter hub 120 before, during, or after the tube deflector 160 is in the open position. The tube deflector 160 can remain in the open position until the deflector arm 166 is forcibly returned back to the closed position. Whether or not the needle assembly 200 has a shield extension 254, the deflector arm 166 can be pivoted manually or passively from the ready to use position past the threshold point to the open position before, during, or after withdrawal of the needle assembly 200 from the catheter hub 120.

With reference again to FIGS. 1, 6A and 6B, the tubing management system 300 comprises a base 434 configured to attach to an open end 127 of the side port 125. The base 434 can comprise a collar 162 having a wall structure defining a hole 163 extending through the collar 162. The open end 127 of the side port 125 can be pressed inside the hole 163 of the collar 162 by interference fit, or attached by mechanical snap fit, adhesive, ultrasonic welding, or other attachment means. The collar 162 can have a chamfer 440 at a proximal end, which can have an angle relative to the opposed end face of the collar 162 so that the surface of the chamfer 440 is substantially co-planar to the proximal end 121 of the catheter hub body 124. This in turn allows the flange 253 of the needle shield 250 to sit flush against the proximal end 121 of the catheter hub body 124, as shown in FIG. 1A.

With reference now to FIGS. 9A-11, an alternative embodiment of a catheter device 10 is shown in accordance with aspects of the present disclosure. The catheter device 10 can be an over-the-needle catheter assembly or an IV catheter assembly comprising a needle assembly 200, a catheter hub 120 having a catheter hub body 124 and a side port 125 extending from the catheter hub body 124, a catheter tube 140 extending distally from the catheter hub body 124, a connector 190, a flexible tubing 180 connected between the connector 190 and the catheter hub 120, a septum 150 located in an interior cavity 123 of the catheter hub body 124 similar to other embodiments discussed elsewhere herein, and a tubing management system 300 for managing the flexible tubing 180, as further discussed below. The embodiments of the catheter device 10 illustrated in FIGS. 9A-11 may be similar to the catheter device illustrated in FIGS. 1A and 1B with a few exceptions.

Figure 10:
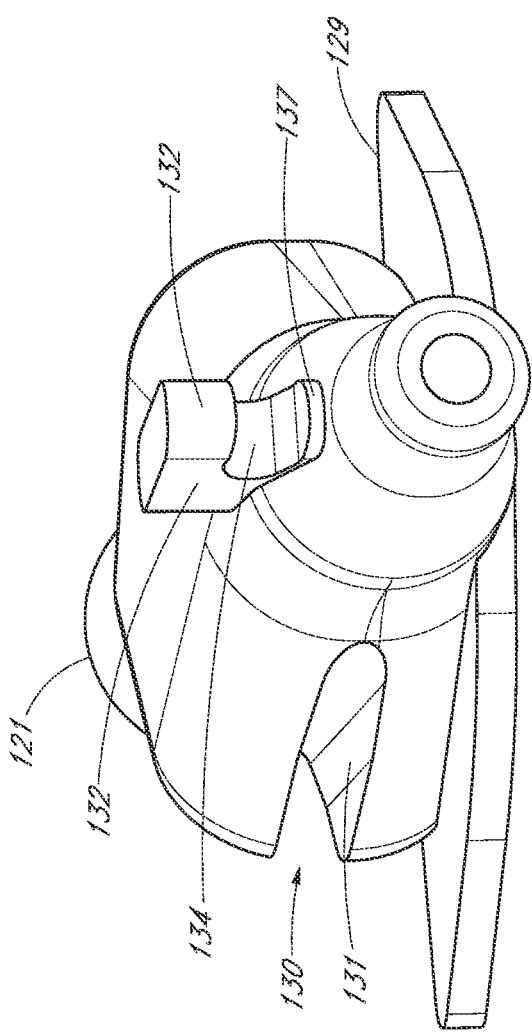
FIG. 10 is an isometric view of the catheter hub of FIG. 9A shown without the flexible tubing and catheter tube for clarity.

With reference to FIGS. 9 and 10, the tubing management system 300 of the present embodiment can comprise a tubing slot 130 on a side of the catheter hub body 124 opposite the location of the side port 125. The tubing slot 130 can secure a portion of the flexible tubing 180 in both the ready to use position and the open position. The tubing slot 130 can be separately formed and subsequently attached to the side of the catheter hub body 124 or can be a groove or slot formed in the side of the catheter hub body 124 opposite the side of the side port 125, such as by molding. The tubing slot 130 is configured to hold the flexible tubing 180 in place thereby forming a U-shaped or J-loop bend 184 between the tubing slot 130 and the proximal end of the side port 125 where the tubing is attached in both the ready to use position and the open position. In one example, the tubing slot 130 can have a cavity 131 sized smaller than a size of the flexible tubing 180 to hold the flexible tubing 180 in place, under a slight interference fit. In another example, the tubing slot 130 can have an opening smaller than a size of the flexible tubing 180 but the cavity 131 can be the same, smaller, or larger in size so that the flexible tubing 180 can be squeezed through the opening and into the cavity 131 of the tubing slot 130.

Also shown in FIGS. 9A, 9B and 10 is a clamp 132 assembly for holding the tubing 180 at a point between the tubing slot 130 and the side port 125. In the present embodiment, a first free end 444 of the tubing 180 is attached to the side port 125. The tubing 180 then forms a first U-shape 184 around a proximal side catheter hub body 124 where it passes through the tubing slot 130 and then extends toward the distal end of the catheter hub body 124 and through the clamp 132 and then back towards the proximal end of the catheter assembly 10 forming a second U-shape bend 183, where it then terminates with the connector 190. A cap 280 with a notch 282, similar to that of FIG. 1C, may be provided at the proximal end of the needle shield 250 to support the tubing and/or the connector 190, as previously discussed. The clamp 132 can be separately formed and subsequently attached to the catheter hub or unitarily formed to a distal portion of the catheter hub 120. The clamp 132 is configured to temporarily hold the flexible tubing 180 in the ready to use position with the connector 190 adjacent the proximal end of the needle shield. In one example, the flexible tubing 180 can be slightly compressed in an interior cavity 139 of the clamp 132 to hold the flexible tubing 180 in place. In another example, the clamp 132 can have an opening 137 slightly smaller than a size of the flexible tubing 180 so that the flexible tubing 180 can be squeezed through the opening 137 and secured inside the interior cavity 139 of the clamp 132 as discussed above and similar to the clamp 168 of FIGS. 6A and 6B.

Figure 11:
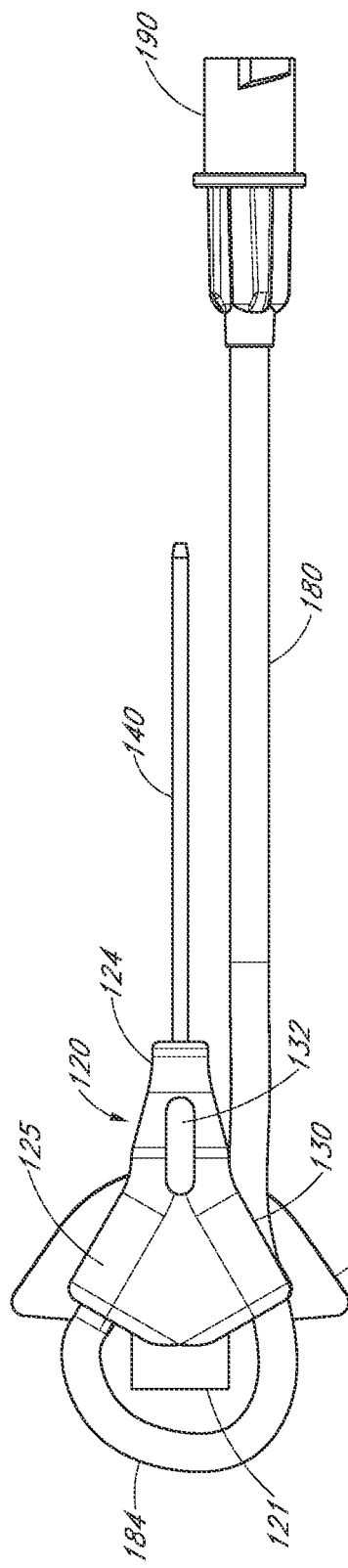
FIG. 11 is a top view of the catheter device of FIG. 9A, shown in an open position with the needle hub removed and the flexible tubing re-positioned.

Referring to FIG. 11, after successful venipuncture, the needle 240 and the needle hub 220 can be retracted proximally away from the catheter hub 120 as previously discussed. The flexible tubing 180 and/or the connector 190 attached to the tubing 180 can be removed from the notch 282 on the cap 280 to move to a used position. The tubing 180 and the connector 190 can be swung in the distal direction from the proximal position to detach from the clamp 132 and move to the open position illustrated in FIG. 11. In the tubing open position of FIG. 11, the tubing slot 130 continues to hold part of the tubing 180 to maintain the first U-shape 184 in the tubing. The connector 190 at the second end 182 of the flexible tubing 180 can be connected to a male Luer connector or other mating connector.

In alternative embodiments, rather than a needle shield, the catheter assembly can incorporate a needle tip protector. The needle tip protector can be positioned inside the catheter hub where the spring clip of FIG. 2 sits and separates from the catheter hub upon retraction of the needle following use, similar to the needle tip protector disclosed in U.S. Pat. No. 8,647,313, the contents of which are expressly incorporated herein by reference.

Methods of making and of using the catheter devices shown and described elsewhere herein are within the scope of the present disclosure.

Although limited embodiments of the catheter devices and their components have been specifically described and illustrated herein, many modifications and variations will be apparent to those skilled in the art. Furthermore, it is understood and contemplated that features specifically discussed for one needle device embodiment may be adopted for inclusion with another needle device embodiment, provided the functions are compatible. For example, release element may be integrated with the needle guard. Accordingly, it is to be understood that the needle devices and their components constructed according to principles of the disclosed device, system, and method may be embodied other than as specifically described herein. The disclosure is also defined in the following claims.

What is claimed is:

1. A catheter device comprising:
    a catheter hub comprising a catheter hub body and a side port with a lumen extending from the catheter hub body, the catheter hub body having a proximal end and a distal end, an interior cavity;
    a catheter tube attached to the distal end of the catheter hub body;
    a septum located in the interior cavity of the catheter hub body between the distal end and the proximal end of the catheter hub body and having an exterior surface sealing against an interior surface of the interior cavity, thereby isolating a distal hub chamber distal of the septum from a proximal hub chamber proximal of the septum, the septum directing fluid flow between the distal hub chamber and the lumen of the side port;
    a needle assembly comprising a needle projecting through the septum and the catheter tube in a ready to use position, the needle having a needle tip extending out a distal end of the catheter tube in the ready to use position, the needle having a proximal end attached to a needle hub;
    a flexible tubing having a lumen and an end connected to an opening of the side port;
    a connector connected to another end of the flexible tubing; and
    a tubing management system comprising a base and a deflector arm hinged to one another, the base having a collar connected to the side port of the catheter hub and the deflector arm comprising a clamp receiving the flexible tubing therein and configured to change direction of the tubing.

2. The catheter device of claim 1, wherein the clamp is a C-shaped clamp having a slot and a length of the flexible tubing passing through the slot to receive the flexible tubing therein.

3. The catheter device of claim 1, wherein the tubing management system further comprises a notch located on the needle assembly and having the flexible tubing received in the notch on the needle assembly to removably hold the flexible tubing in the ready to use position.

4. The catheter device of claim 1, wherein the base has a chamfer.

5. The catheter device of claim 1, further comprising a needle shield having an elongated body and a spring clip with a surface attached to the elongated body, the surface of the spring clip to be located distally of the needle tip in a needle retracted position.

6. The catheter device of claim 5, wherein the needle shield comprises a flange, a proximal portion having a length extending proximally of the flange, and a distal portion having a length extending distally of the flange, and wherein the length of the proximal portion is longer than the length of the distal portion.

7. The catheter device of claim 6, wherein the spring clip is located in a hollow space of the distal portion.

8. A catheter device comprising:
a catheter hub comprising a catheter hub body and a side port extending from the catheter hub body, the catheter hub body having a proximal end and a distal end, an interior cavity, the side port having a lumen;
a catheter tube attached to the distal end of the catheter hub body;
a septum located in the interior cavity of the catheter hub body between the distal end and the proximal end of the catheter hub body, thereby isolating a distal hub chamber distal of the septum from a proximal hub chamber proximal of the septum, the septum preventing fluid flow between the distal hub chamber and the proximal hub chamber, the septum directing fluid flow between the distal hub chamber and the lumen of the side port;
a needle assembly comprising a needle projecting through the septum and the catheter tube in a ready to use position, the needle having a needle tip extending out a distal end of the catheter tube in the ready to use position, the needle having a proximal end attached to a needle hub;
a flexible tubing having an end coupled to an opening of the side port;
a connector coupled to another end of the flexible tubing;
a tubing management system configured to bend the flexible tubing, the tubing management system comprising a clamp coupled to the catheter hub and receiving the flexible tubing therein; and
wherein the tubing management system further comprises a tube deflector comprising a deflector arm pivotably coupled to the side port from the ready to use position to an open position, the deflector arm resisting pivoting from the ready to use position to the open position until the deflector arm is pivoted beyond a threshold pivot point, the deflector arm comprising the clamp.

9. The catheter device of claim 8, wherein the needle assembly is in contact with the deflector arm of the tube deflector from the ready to use position past the threshold point to the open position during withdrawal of the needle assembly from the catheter hub.

10. The catheter device of claim 8, wherein the tube deflector further comprises a fixed side attached to an open end of the side port, the deflector arm pivotably attached to the fixed side by a hinge.

11. The catheter device of claim 10, wherein the fixed side is attached to the open end of the side port by mechanical snap fit, adhesive, or ultrasonic welding.

12. The catheter device of claim 10, wherein the fixed side comprises a collar, a collar hole is defined through the collar, and the proximal end of the port is received in the collar hole.

13. The catheter device of claim 12, wherein the collar has a chamfer at a proximal end of the collar substantially coplanar with the proximal end of the catheter hub body.

14. A catheter device comprising:
a catheter hub comprising a catheter hub body and a side port with a lumen extending from the catheter hub body, the catheter hub body having a proximal end and a distal end, an interior cavity;
a catheter tube attached to the distal end of the catheter hub body;
a septum located in the interior cavity of the catheter hub body between the distal end and the proximal end of the catheter hub body and having an exterior surface sealing against an interior surface of the interior cavity, thereby isolating a distal hub chamber distal of the septum from a proximal hub chamber proximal of the septum, the septum directing fluid flow between the distal hub chamber and the lumen of the side port;
a needle assembly comprising a needle projecting through the septum and the catheter tube in a ready to use position, the needle having a needle tip extending out a distal end of the catheter tube in the ready to use position, the needle having a proximal end attached to a needle hub;
a flexible tubing having a lumen and an end connected to an opening of the side port;
a connector connected to another end of the flexible tubing;
a tubing management system directly connected to the catheter hub or formed with the catheter hub, the tubing management system comprising a clamp receiving the flexible tubing therein;
a needle shield comprising an elongated body having a hollow interior and a distal portion projecting into the proximal end of the catheter hub body; and
wherein the needle hub comprises a needle holder with a bore holding the proximal end of the needle located within the hollow interior of the needle shield and the needle hub comprises a shroud surround at least part of an exterior of the elongated body of the needle shield.

15. The catheter device of claim 14, wherein the needle shield comprises a lengthwise slot and the needle hub has a tab located in the slot of the needle shield and tab connecting the needle holder and the shroud.

16. The catheter device of claim 14, further comprising a spring clip comprising a wall with an opening, and wherein the spring clip is located in a hollow space of the distal portion of the needle shield.

17. The catheter device of claim 14, wherein the tubing management system comprises a base and a deflector arm hinged to one another, the base having a collar receiving the side port therein and the deflector arm comprising a clamp receiving the flexible tubing therein.

18. The catheter device of claim 14, wherein the clamp is unitarily formed to an exterior surface of the catheter hub.

19. The catheter device of claim 18, further comprising a tubing slot having a cavity formed with the catheter hub and spaced from the clamp, the cavity of the tubing slot having a section of the tubing located therein.

* * * * *